United States Patent
Sisk

(10) Patent No.: US 9,978,953 B2
(45) Date of Patent: *May 22, 2018

(54) SUBSTITUTED BIPHENYL COMPOUNDS FOR USE IN LIGHT-EMITTING DEVICES

(71) Applicant: Nitto Denko Corporation, Osaka (JP)

(72) Inventor: David T. Sisk, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 696 days.

This patent is subject to a terminal disclaimer.

(21) Appl. No.: 14/011,597

(22) Filed: Aug. 27, 2013

(65) Prior Publication Data

US 2014/0061620 A1 Mar. 6, 2014

Related U.S. Application Data

(60) Provisional application No. 61/696,035, filed on Aug. 31, 2012.

(51) Int. Cl.
| | | |
|---|---|---|
| *H01L 51/00* | (2006.01) | |
| *H01L 51/52* | (2006.01) | |
| *C07D 263/57* | (2006.01) | |
| *C07D 277/66* | (2006.01) | |

(52) U.S. Cl.
CPC ........ *H01L 51/0071* (2013.01); *C07D 263/57* (2013.01); *C07D 277/66* (2013.01); *H01L 51/52* (2013.01); *H01L 51/5268* (2013.01)

(58) Field of Classification Search
CPC . C07D 263/57; C07D 277/66; H01L 51/0071; H01L 51/52; H01L 151/5268; C09K 11/06
See application file for complete search history.

(56) References Cited

U.S. PATENT DOCUMENTS

| | | | |
|---|---|---|---|
| 5,536,588 A * | 7/1996 | Naito | C09K 11/06 136/263 |
| 6,354,709 B1 | 3/2002 | Campbell et al. | |
| 6,594,079 B1 | 7/2003 | Trott et al. | |
| 6,707,611 B2 | 3/2004 | Gardiner et al. | |
| 7,799,416 B1 | 9/2010 | Chan et al. | |
| 7,864,450 B2 | 1/2011 | Segawa et al. | |
| 7,957,621 B2 | 6/2011 | Zhang et al. | |
| 8,952,364 B2 * | 2/2015 | Lai | H01L 51/5268 257/40 |
| 2003/0219625 A1 * | 11/2003 | Wolk | C09K 11/06 428/690 |

(Continued)

OTHER PUBLICATIONS

Shao et al., Inorganic Chemistry, (2012), vol. 51, pp. 4343-4351.*

*Primary Examiner* — Dawn L Garrett
(74) *Attorney, Agent, or Firm* — K&L Gates LLP; Louis C. Cullman; Robert W. Winn

(57) ABSTRACT

This disclosure relates to compounds for use in light-emitting devices are described herein. These compounds may include a biphenyl that includes four substituents, such as benzoxazolyl, benzothiazolyl, or benzimidazolyl substituents, such as a compound represented by Formula 1. These compounds can incorporated into a nanostructure material or a plurality of nanostructures, which can be useful for light-scattering or light-extraction, for example, to increase the efficiency of light-emitting devices.

19 Claims, 4 Drawing Sheets

(56) References Cited

U.S. PATENT DOCUMENTS

| | | | |
|---|---|---|---|
| 2004/0124766 A1* | 7/2004 | Nakagawa | H01L 51/0064 313/504 |
| 2004/0150328 A1* | 8/2004 | Czerw | B82Y 10/00 313/506 |
| 2005/0019602 A1* | 1/2005 | Sellinger | B82Y 20/00 428/690 |
| 2006/0105200 A1* | 5/2006 | Poplavskyy | B82Y 10/00 428/690 |
| 2008/0007157 A1* | 1/2008 | Carroll | B82Y 10/00 313/504 |
| 2011/0140093 A1 | 6/2011 | Zheng et al. | |
| 2012/0223635 A1* | 9/2012 | Mochizuki | H01L 51/5268 313/512 |
| 2012/0226046 A1* | 9/2012 | Zheng | C07D 263/64 546/256 |
| 2015/0228907 A1* | 8/2015 | Ma | H01L 51/005 428/143 |

* cited by examiner

| LiF (1)/Al (100) | ~590 |
| TPBI (40 nm) | ~580 |
| TBB (0.4 nm) | ~560 |
| Host-2:Ir(plq)acac(30, 10wt%) | ~550 |
| NPB (30) | ~540 |
| PEDOT (40) | ~530 |
| ITO (110) | ~520 |
| glass | ~510 |

FIG. 4

| Mg: Ag (20 nm, 1:3) | |
| LiF (1 nm) | ~590 |
| TPBI (40 nm) | ~580 |
| TBB (0.4 nm) | ~560 |
| Host-2:Ir(plq)acac(20, 10wt%) | ~550 |
| NPB (40 nm) | ~540 |
| $MoO_3$ (10 nm) | ~530 |
| SiN (40 nm) | ~520 |
| glass | ~510 |

FIG. 5

SUBSTITUTED BIPHENYL COMPOUNDS FOR USE IN LIGHT-EMITTING DEVICES

CROSS REFERENCE TO RELATED APPLICATIONS

The present application claims the benefit under 35 U.S.C. § 119(e) to U.S. Provisional Application Ser. No. 61/696,035 filed Aug. 31, 2012, the entire contents of which are hereby incorporated by reference in their entirety.

SUMMARY

Compounds for use in light-emitting devices are described herein. These compounds may include a biphenyl that includes four substituents, such as benzoxazolyl, benzothiazolyl, or benzimidazolyl substituents.

Some embodiments include a compound represented by Formula 1:

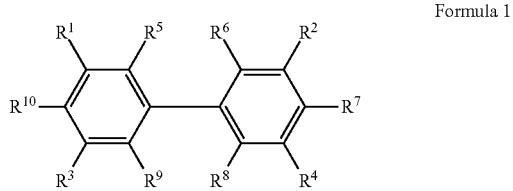

Formula 1 wherein $R^1$, $R^2$, $R^3$, and $R^4$ are independently optionally substituted benzoxazol-2-yl, optionally substituted benzothiazol-2-yl, or optionally substituted benzimidazol-2-yl; and $R^5$, $R^6$, $R^7$, $R^8$, $R^9$, and $R^{10}$ are independently H or substituents.

In some embodiments, $R^1$, $R^2$, $R^3$, and $R^4$ are independently optionally substituted benzoxazol-2-yl, optionally substituted benzothiazol-2-yl, or optionally substituted benzimidazol-2-yl, wherein any substituents of benzoxazol-2-yl, benzothiazol-2-yl, or benzimidazoly-2-yl are independently F, Cl, $CH_3$, $CF_3$, CN, $OCH_3$, $NH_2$, $NO_2$, $CO_2H$, CHO, or OH; and $R^5$, $R^6$, $R^7$, $R^8$, $R^9$, and $R^{10}$ are independently H, F, Cl, $CH_3$, $CF_3$, CN, $OCH_3$, $NH_2$, $NO_2$, $CO_2H$, CHO (formyl), or OH.

The compounds described herein may be used in light-emitting devices as a nanostructure material or a plurality of nanostructures, a light-extracting material, or both.

Some embodiments include a nanostructure material or a plurality of nanostructures comprising a compound described herein.

Some embodiments include a nanostructure material comprising a compound described herein.

Some embodiments include a nanostructure composition comprising a compound described herein.

Some embodiments include a light-emitting device comprising an anode, a cathode, a light-emitting layer disposed between the anode and the cathode, and a compound described herein. In some embodiments, the compound is part of a nanostructure material disposed between the anode and the cathode. In some embodiments, the device has improved efficiency as compared to a device that is identical in all respects except that it contains no nanostructure material. In some embodiments, the compound is part of a light-extracting material, wherein the anode or the cathode is disposed between the light-emitting layer and the light-extracting material. In some embodiments, the device has improved efficiency as compared to a device that is identical in all respects except that it contains no light-extracting material.

BRIEF DESCRIPTION OF THE DRAWINGS

FIG. 4 is a schematic depiction of an embodiment of an organic light-emitting device.

FIG. 5 is a schematic depiction of an embodiment of an organic light-emitting device.

DETAILED DESCRIPTION

Figure 1:
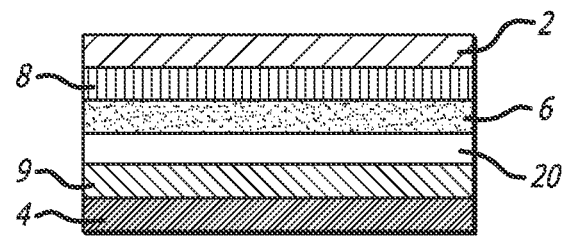
FIG. 1 is a schematic depiction of an embodiment of an organic light-emitting device.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-5 or 0-2 carbon atoms; and 0-5 or 0-3 heteroatoms, wherein each heteroatom may independently be: N, O, S, Si, F, Cl, Br, or I; provided that the substituent includes at least one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by |, attachment may occur at any position normally occupied by a hydrogen atom.

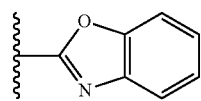

Benzoxazol-2-yl

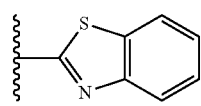

Benzothiazol-2-yl

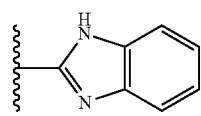

Benzimidazol-2-yl

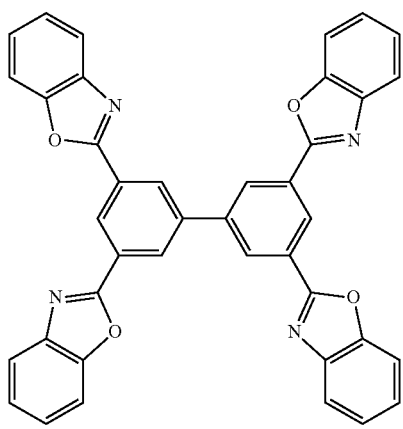

3,5,3',5'-tetra(benzoxazol-2-yl)biphenyl (TBB)

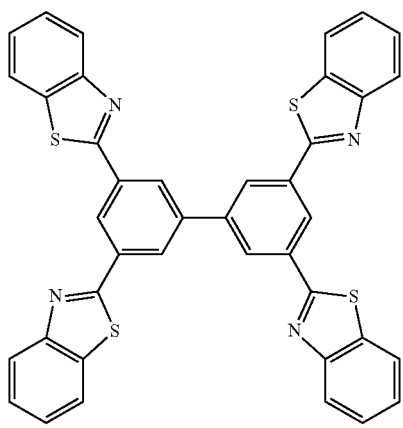

3,5,3',5'-tetra(benzothiazol-2-yl)biphenyl

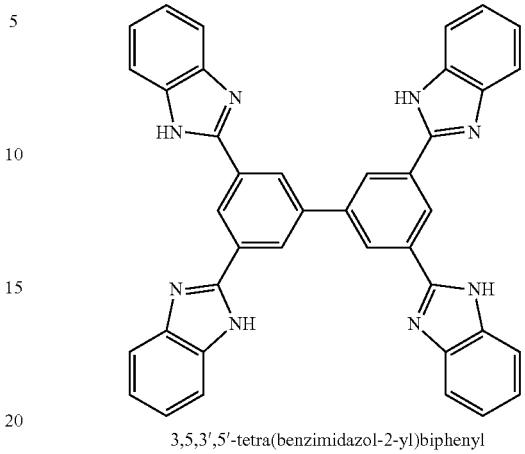

3,5,3',5'-tetra(benzimidazol-2-yl)biphenyl

Some embodiments include optionally substituted 3,5,3',5'-tetra(benzoxazol-2-yl)biphenyl; optionally substituted 3,5,3',5'-tetra(benzothiazol-2-yl)biphenyl; or optionally substituted 3,5,3',5'-tetra(benzoimidazol-2-yl)biphenyl.

Formula 2

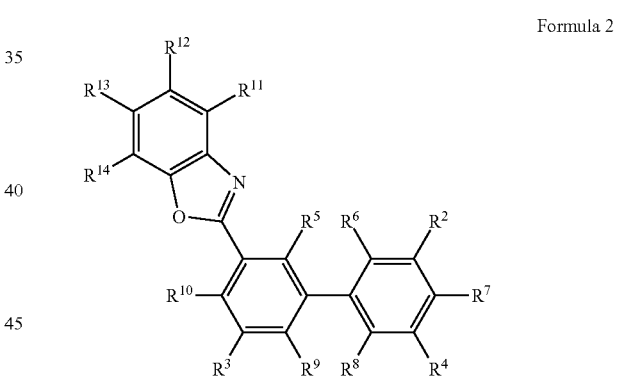

Formula 3

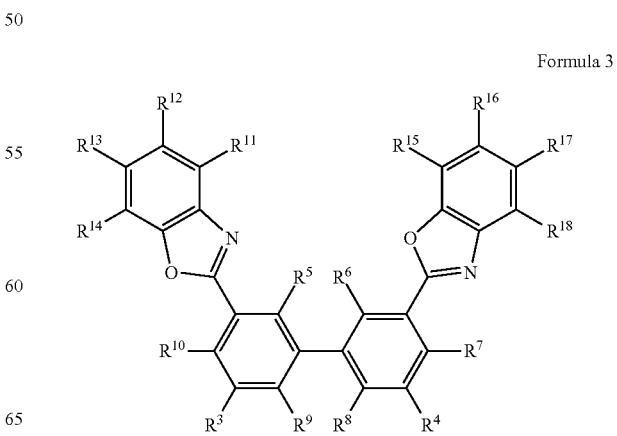

Formula 4
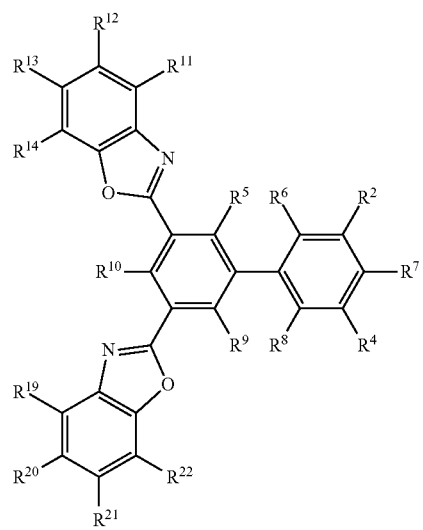
Formula 5
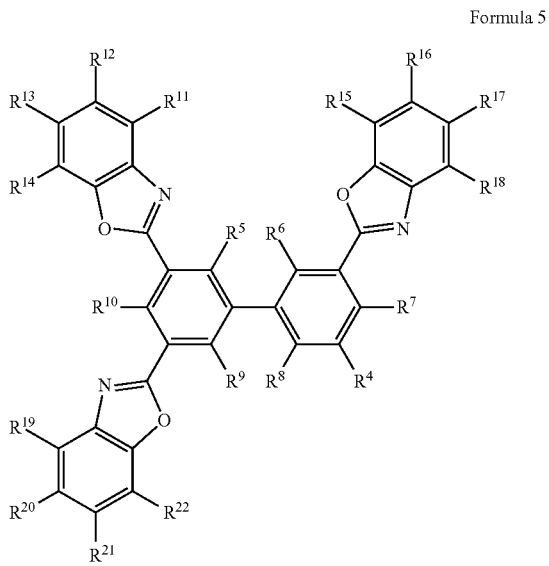
Formula 6
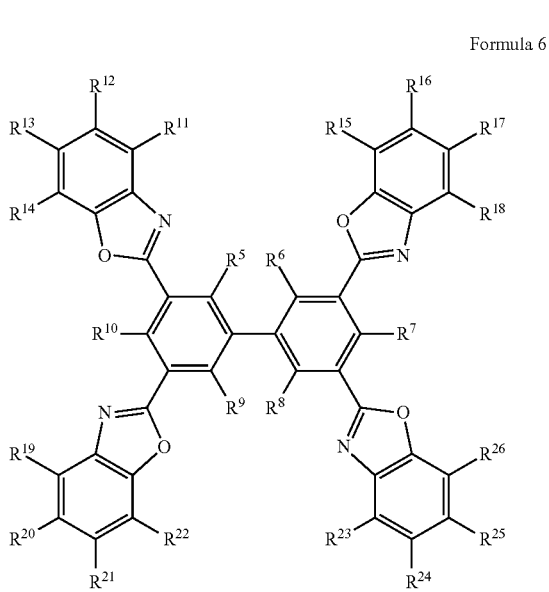
Formula 7
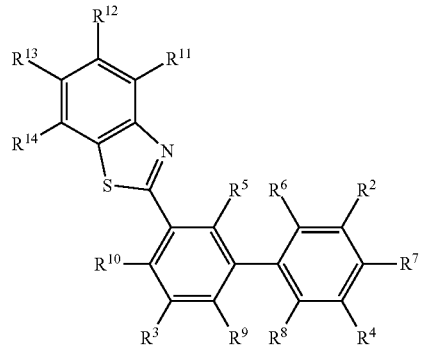
Formula 8
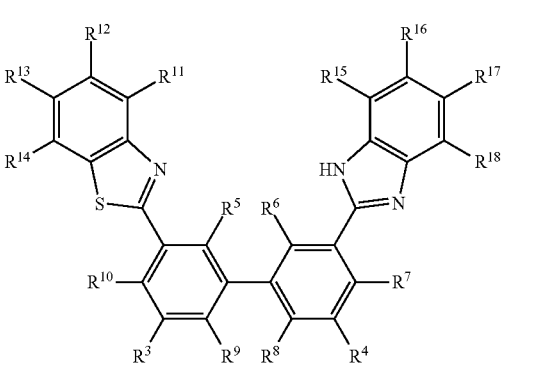
Formula 9
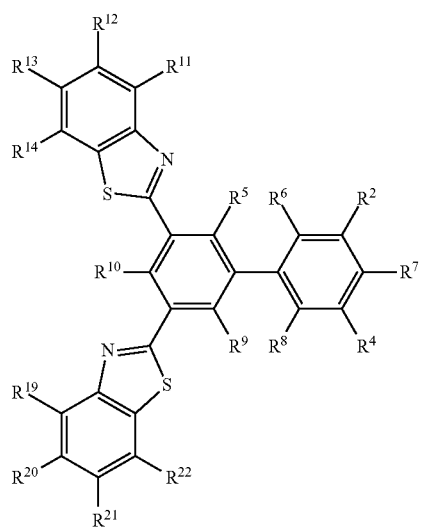

Formula 10
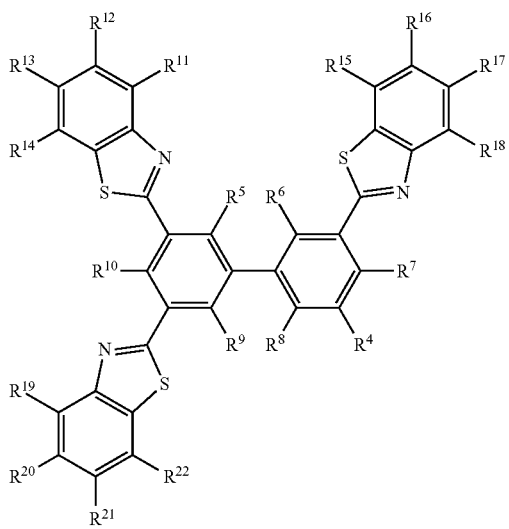
Formula 11
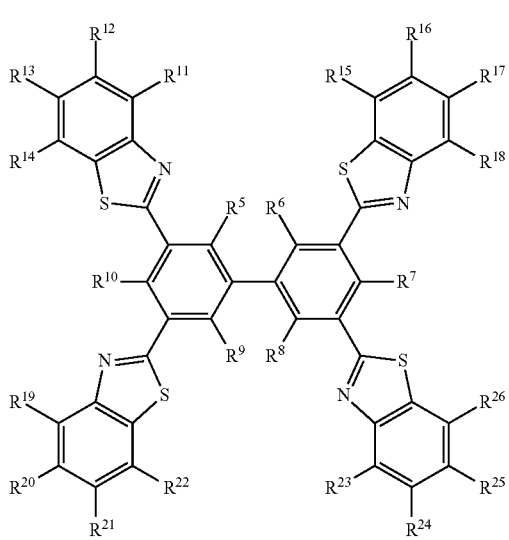
Formula 12
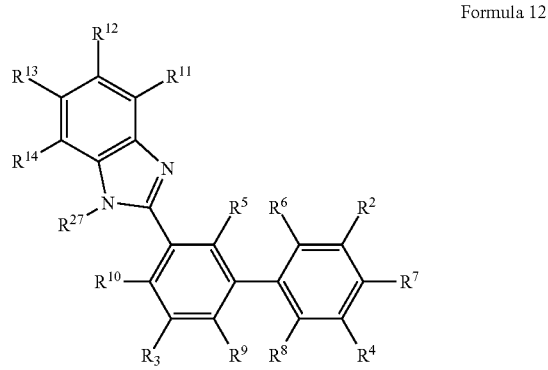
Formula 13
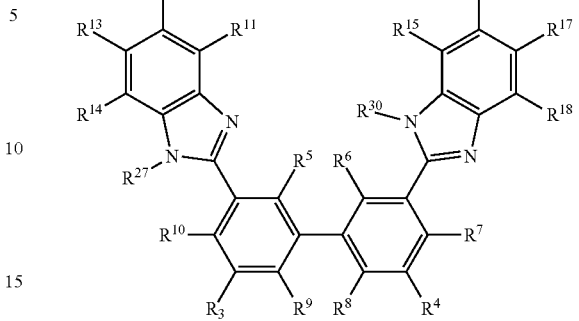
Formula 14
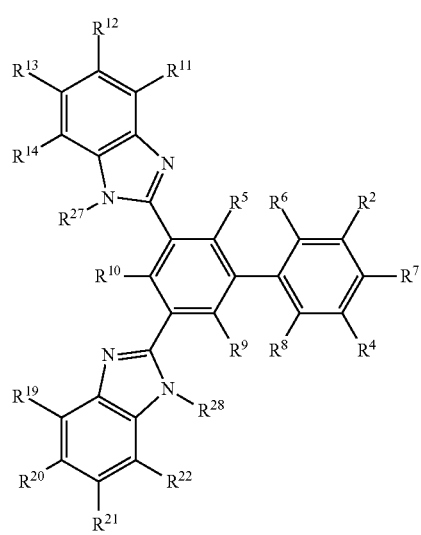
Formula 15
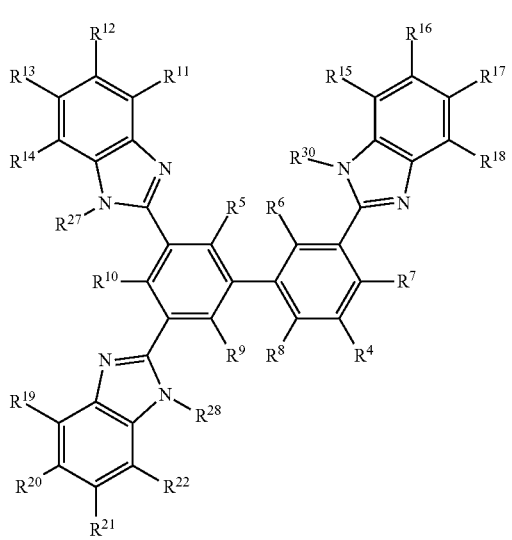

-continued

Formula 16

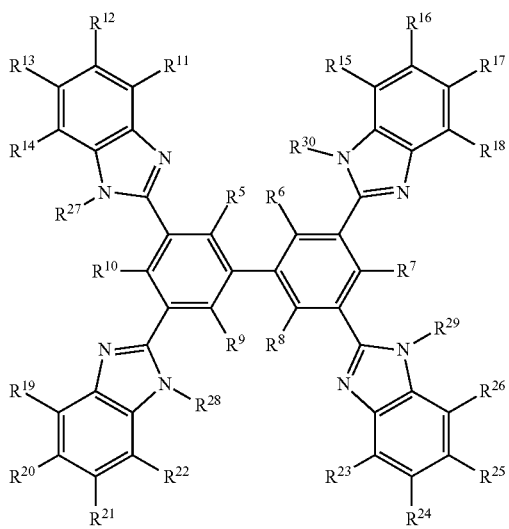

With respect to any relevant formula or structural representation herein, such as Formula 1, $R^1$ may be optionally substituted benzoxazol-2-yl, optionally substituted benzothiazol-2-yl, or optionally substituted benzimidazol-2-yl. In some embodiments, any substituents of benzoxazol-2-yl, benzothiazol-2-yl, or benzimidazol-2-yl are independently F, Cl, $CH_3$, $CF_3$, CN, $OCH_3$, $NH_2$, $NO_2$, $CO_2H$, CHO, or OH. In some embodiments, any substituents of benzoxazol-2-yl, benzothiazol-2-yl, or benzimidazoly-2-yl are F or Cl. In some embodiments, the benzoxazol-2-yl, the benzothiazol-2-yl, or the benzimidazol-2-yl is unsubstituted.

In some embodiments, $R^1$ is

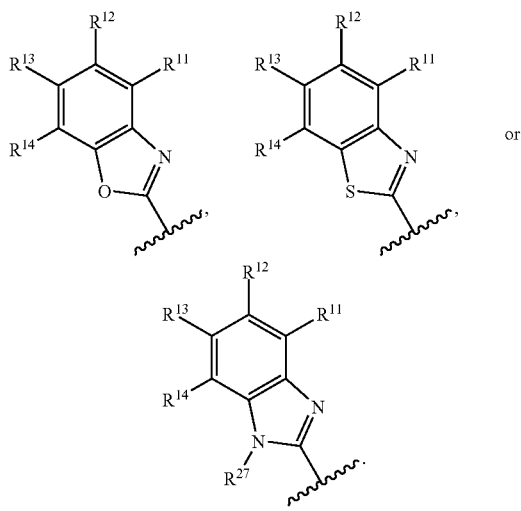

With respect to any relevant formula or structural representation herein, such as Formulas 1, 2, 4, 7, 9, 12, and 14, $R^2$ may be optionally substituted benzoxazol-2-yl, optionally substituted benzothiazol-2-yl, or optionally substituted benzimidazol-2-yl. In some embodiments, any substituents of benzoxazol-2-yl, benzothiazol-2-yl, or benzimidazol-2-yl are independently F, Cl, $CH_3$, $CF_3$, CN, $OCH_3$, $NH_2$, $NO_2$, $CO_2H$, CHO, or OH. In some embodiments, any substituents of benzoxazol-2-yl, benzothiazol-2-yl, or benzimidazoly-2-yl are F or Cl. In some embodiments, the benzoxazol-2-yl, the benzothiazol-2-yl, or the benzimidazol-2-yl is unsubstituted.

In some embodiments, $R^2$ is

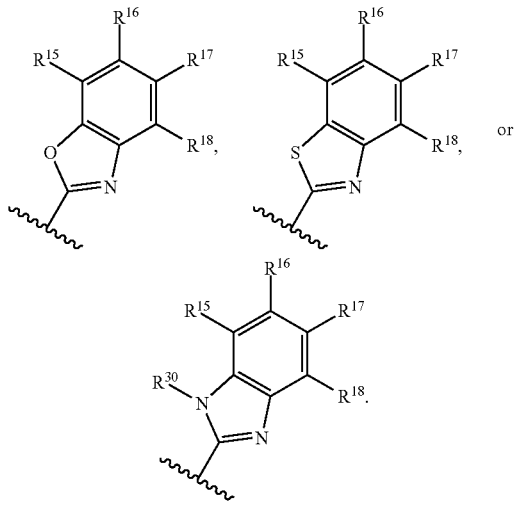

With respect to any relevant formula or structural representation herein, such as Formulas 1, 2, 3, 7, 8, 12, and 13, $R^3$ may be optionally substituted benzoxazol-2-yl, optionally substituted benzothiazol-2-yl, or optionally substituted benzimidazol-2-yl. In some embodiments, any substituents of benzoxazol-2-yl, benzothiazol-2-yl, or benzimidazol-2-yl are independently F, Cl, $CH_3$, $CF_3$, CN, $OCH_3$, $NH_2$, $NO_2$, $CO_2H$, CHO, or OH. In some embodiments, any substituents of benzoxazol-2-yl, benzothiazol-2-yl, or benzimidazoly-2-yl are F or Cl. In some embodiments, the benzoxazol-2-yl, the benzothiazol-2-yl, or the benzimidazol-2-yl is unsubstituted.

In some embodiments, $R^3$ is

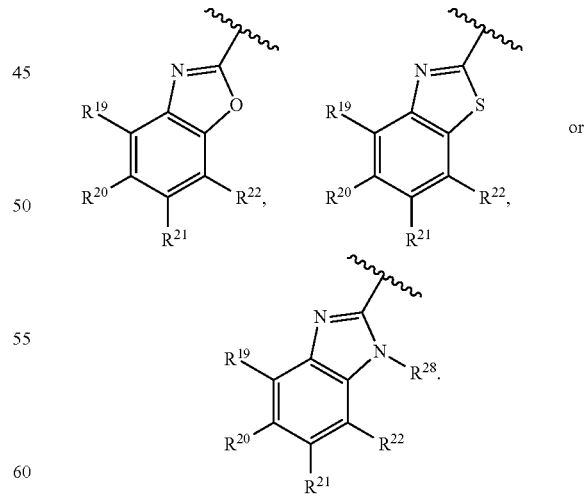

With respect to any relevant formula or structural representation herein, such as Formulas 1-5, 7-10, and 12-15, $R^4$ may be optionally substituted benzoxazol-2-yl, optionally substituted benzothiazol-2-yl, or optionally substituted benzimidazol-2-yl. In some embodiments, any substituents of benzoxazol-2-yl, benzothiazol-2-yl, or benzimidazol-2-yl are independently F, Cl, $CH_3$, $CF_3$, CN, $OCH_3$, $NH_2$, $NO_2$, $CO_2H$, CHO, or OH. In some embodiments, any substituents of benzoxazol-2-yl, benzothiazol-2-yl, or benzimidazoly-2-yl are F or Cl. In some embodiments, the benzoxazol-2-yl, the benzothiazol-2-yl, or the benzimidazol-2-yl is unsubstituted.

In some embodiments, $R^4$ is

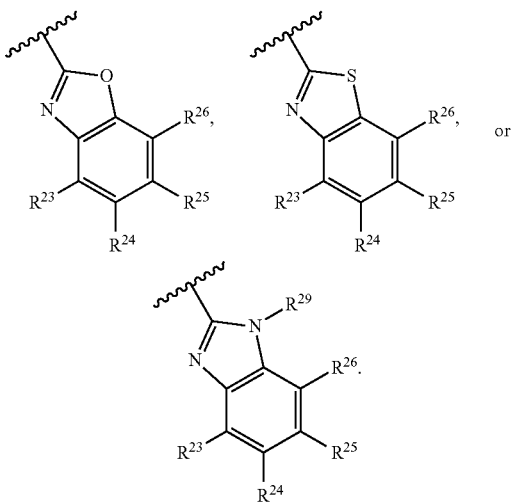

With respect to any relevant formula or structural representation herein, such as Formulas 1-16, $R^5$ may be H, or any substituent, such as F, Cl, $CH_3$, $CF_3$, CN, $OCH_3$, $NH_2$, $NO_2$, $CO_2H$, CHO, or OH. In some embodiments, $R^5$ is H, F, $CF_3$, CN, CHO, or OH. In some embodiments, $R^5$ is H.

With respect to any relevant formula or structural representation herein, such as Formulas 1-16, $R^6$ may be H, or any substituent, such as F, Cl, $CH_3$, $CF_3$, CN, $OCH_3$, $NH_2$, $NO_2$, $CO_2H$, CHO, or OH. In some embodiments, $R^6$ is H, F, or CN. In some embodiments, $R^6$ is H.

With respect to any relevant formula or structural representation herein, such as Formulas 1-16, $R^7$ may be H, or any substituent, such as F, Cl, $CH_3$, $CF_3$, CN, $OCH_3$, $NH_2$, $NO_2$, $CO_2H$, CHO, or OH. In some embodiments, $R^7$ is H, F, $CF_3$, CN, $OCH_3$, $NH_2$, $CO_2H$, CHO, or OH. In some embodiments, $R^7$ is H.

With respect to any relevant formula or structural representation herein, such as Formulas 1-16, $R^8$ may be H, or any substituent, such as F, Cl, $CH_3$, $CF_3$, CN, $OCH_3$, $NH_2$, $NO_2$, $CO_2H$, CHO, or OH. In some embodiments, $R^8$ is H, or F. In some embodiments, $R^8$ is H.

In some embodiments, $R^6$ and $R^7$ are H. In some embodiments, $R^6$, $R^7$, and $R^8$ are H.

With respect to any relevant formula or structural representation herein, such as Formulas 1-16, $R^9$ may be H, or any substituent, such as F, Cl, $CH_3$, $CF_3$, CN, $OCH_3$, $NH_2$, $NO_2$, $CO_2H$, CHO, or OH. In some embodiments, $R^9$ is H.

With respect to any relevant formula or structural representation herein, such as Formulas 1-16, $R^{10}$ may be H, or any substituent, such as F, Cl, $CH_3$, $CF_3$, CN, $OCH_3$, $NH_2$, $NO_2$, $CO_2H$, CHO, or OH. In some embodiments, $R^{10}$ is H, F, $CF_3$, CN, $OCH_3$, $NH_2$, $CO_2H$, CHO, or OH. In some embodiments, $R^{10}$ is H.

In some embodiments, $R^5$ and $R^{10}$ are H. In some embodiments, $R^5$, $R^9$, and $R^{10}$ are H.

With respect to any relevant formula or structural representation herein, such as Formulas 2-16, $R^{11}$ may be H, or any substituent, such as F, Cl, $CH_3$, $CF_3$, CN, $OCH_3$, $NH_2$, $NO_2$, $CO_2H$, CHO, or OH. In some embodiments, $R^{11}$ is H, F, $CF_3$, CN, or $CO_2H$. In some embodiments, $R^{11}$ is H.

With respect to any relevant formula or structural representation herein, such as Formulas 2-16, $R^{12}$ may be H, or any substituent, such as F, Cl, $CH_3$, $CF_3$, CN, $OCH_3$, $NH_2$, $NO_2$, $CO_2H$, CHO, or OH. In some embodiments, $R^{12}$ is H, F, $CF_3$, CN, or OH. In some embodiments, $R^{12}$ is H.

With respect to any relevant formula or structural representation herein, such as Formulas 2-16, $R^{13}$ may be H, or any substituent, such as F, Cl, $CH_3$, $CF_3$, CN, $OCH_3$, $NH_2$, $NO_2$, $CO_2H$, CHO, or OH. In some embodiments, $R^{13}$ is H, F, $CF_3$, $OCH_3$, $NH_2$, $CO_2H$, or OH. In some embodiments, $R^{13}$ is H.

With respect to any relevant formula or structural representation herein, such as Formulas 2-16, $R^{14}$ may be H, or any substituent, such as F, Cl, $CH_3$, $CF_3$, CN, $OCH_3$, $NH_2$, $NO_2$, $CO_2H$, CHO, or OH. In some embodiments, $R^{14}$ is H, F, $CF_3$, or CN. In some embodiments, $R^{14}$ is H.

In some embodiments, $R^{11}$ and $R^{12}$ are H. In some embodiments, $R^{11}$, $R^{12}$, $R^{13}$ and $R^{14}$ are H.

With respect to any relevant formula or structural representation herein, such as Formulas 3, 5, 6, 8, 10, 11, 13, 15, and 16, $R^{15}$ may be H, or any substituent, such as F, Cl, $CH_3$, $CF_3$, CN, $NO_2$, $CO_2H$, or OH. In some embodiments, $R^{15}$ is H, F, $CF_3$, or CN. In some embodiments, $R^{15}$ is H or F. In some embodiments, $R^{15}$ is H.

With respect to any relevant formula or structural representation herein, such as Formulas 3, 5, 6, 8, 10, 11, 13, 15, and 16, $R^{16}$ may be H, or any substituent, such as F, Cl, $CH_3$, $CF_3$, CN, $NO_2$, $CO_2H$, or OH. In some embodiments, $R^{16}$ is H, F, $CF_3$, or CN. In some embodiments, $R^{16}$ is H or $CF_3$. In some embodiments, $R^{16}$ is H.

With respect to any relevant formula or structural representation herein, such as Formulas 3, 5, 6, 8, 10, 11, 13, 15, and 16, $R^{17}$ may be H, or any substituent, such as F, Cl, $CH_3$, $CF_3$, CN, $NO_2$, $CO_2H$, or OH. In some embodiments, $R^{17}$ is H, F, $CF_3$, or CN. In some embodiments, $R^{17}$ is H or $CH_3$. In some embodiments, $R^{17}$ is H.

With respect to any relevant formula or structural representation herein, such as Formulas 3, 5, 6, 8, 10, 11, 13, 15, and 16, $R^{18}$ may be H, or any substituent, such as F, Cl, $CH_3$, $CF_3$, CN, $NH_2$, $NO_2$, or OH. In some embodiments, $R^{18}$ is H, F, $CF_3$, or CN. In some embodiments, $R^{18}$ is H, F, or $CF_3$. In some embodiments, $R^{18}$ is H.

In some embodiments, $R^{15}$ and $R^{17}$ are H. In some embodiments, $R^{15}$, $R^{16}$, $R^{17}$ and $R^{18}$ are H.

With respect to any relevant formula or structural representation herein, such as Formulas 4-6, 9-11, and 14-16, $R^{19}$ may be H, or any substituent, such as F, Cl, $CH_3$, $CF_3$, CN, $NH_2$, $NO_2$, or OH. In some embodiments, $R^{19}$ is H, F, $CF_3$, $CH_3$, or CN. In some embodiments, $R^{19}$ is H, F, or $CH_3$. In some embodiments, $R^{19}$ is H.

With respect to any relevant formula or structural representation herein, such as Formulas 4-6, 9-11, and 14-16, $R^{20}$ may be H, or any substituent, such as F, Cl, $CH_3$, $CF_3$, CN, $NH_2$, $NO_2$, or OH. In some embodiments, $R^{20}$ is H, F, $CF_3$, $CH_3$, or CN. In some embodiments, $R^{20}$ is H, F, or $CF_3$. In some embodiments, $R^{20}$ is H.

With respect to any relevant formula or structural representation herein, such as Formulas 4-6, 9-11, and 14-16, $R^{21}$ may be H, or any substituent, such as F, Cl, $CH_3$, $CF_3$, CN, $NH_2$, $NO_2$, or OH. In some embodiments, $R^{21}$ is H, F, $CF_3$, $CH_3$, or CN. In some embodiments, $R^{21}$ is H or F. In some embodiments, $R^{21}$ is H.

With respect to any relevant formula or structural representation herein, such as Formulas 4-6, 9-11, and 14-16, $R^{22}$ may be H, or any substituent, such as F, Cl, $CH_3$, $CF_3$, CN, $NH_2$, $NO_2$, or OH. In some embodiments, $R^{22}$ is H, F, $CF_3$, $CH_3$, or CN. In some embodiments, $R^{22}$ is H, or $CF_3$. In some embodiments, $R^{22}$ is H.

In some embodiments, $R^{19}$ and $R^{22}$ are H. In some embodiments, $R^{19}$, $R^{20}$, $R^{21}$ and $R^{22}$ are H.

With respect to any relevant formula or structural representation herein, such as Formulas 6, 11, and 16, $R^{23}$ may be H, or any substituent, such as F, Cl, $CH_3$, $CF_3$, $CF_2CF_3$, CN, $NH_2$, $NO_2$, or OH. In some embodiments, $R^{23}$ is H, F, $CF_3$, $CH_3$, or CN. In some embodiments, $R^{23}$ is H, F, or $CH_3$. In some embodiments, $R^{23}$ is H.

With respect to any relevant formula or structural representation herein, such as Formulas 6, 11, and 16, $R^{24}$ may be H, or any substituent, such as F, Cl, $CH_3$, $CF_3$, $CF_2CF_3$, CN, $NH_2$, $NO_2$, or OH. In some embodiments, $R^{24}$ is H, F, $CF_3$, $CH_3$, or CN. In some embodiments, $R^{24}$ is H, F, or $CF_3$. In some embodiments, $R^{24}$ is H.

With respect to any relevant formula or structural representation herein, such as Formulas 6, 11, and 16, $R^{25}$ may be H, or any substituent, such as F, Cl, $CH_3$, $CF_3$, $CF_2CF_3$, CN, $NH_2$, $NO_2$, or OH. In some embodiments, $R^{25}$ is H, F, $CF_3$, $CH_3$, or CN. In some embodiments, $R^{25}$ is H or F. In some embodiments, $R^{25}$ is H.

With respect to any relevant formula or structural representation herein, such as Formulas 6, 11, and 16, $R^{26}$ may be H, or any substituent, such as F, Cl, $CH_3$, $CF_3$, $CF_2CF_3$, CN, $NH_2$, $NO_2$, or OH. In some embodiments, $R^{26}$ is H, F, $CF_3$, $CH_3$, or CN. In some embodiments, $R^{26}$ is H, or $CF_3$. In some embodiments, $R^{26}$ is H.

In some embodiments, $R^{11}$, $R^{18}$, $R^{23}$, and $R^{28}$ are H. In some embodiments, $R^{12}$, $R^{17}$, $R^{20}$, and $R^{24}$ are H. In some embodiments, $R^{13}$, $R^{16}$, $R^{21}$, and $R^{25}$ are H. In some embodiments, $R^{14}$, $R^{15}$, $R^{22}$, and $R^{26}$ are H.

With respect to any relevant formula or structural representation herein, such as Formulas 13-16, in some embodiments, $R^{27}$ may be H, or any substituent, such as $CH_3$, $CH_2CH_3$, or optionally substituted phenyl. In some embodiments, $R^{27}$ is H, or phenyl optionally substituted with F, $CF_3$, $CH_3$, CN, or a combination thereof. In some embodiments, $R^{27}$ is unsubstituted phenyl. In some embodiments, $R^{27}$ is H.

With respect to any relevant formula or structural representation herein, such as Formulas 12-16, in some embodiments, $R^{28}$ may be H, or any substituent, such as $CH_3$, $CH_2CH_3$, or optionally substituted phenyl. In some embodiments, $R^{28}$ is H, or phenyl optionally substituted with F, $CF_3$, $CH_3$, CN, or a combination thereof. In some embodiments, $R^{28}$ is unsubstituted phenyl. In some embodiments, $R^{28}$ is H.

With respect to any relevant formula or structural representation herein, such as Formula 16, in some embodiments, $R^{29}$ may be H, or any substituent, such as $CH_3$, $CH_2CH_3$, or optionally substituted phenyl. In some embodiments, $R^{29}$ is H, or phenyl optionally substituted with F, $CF_3$, $CH_3$, ON, or a combination thereof. In some embodiments, $R^{29}$ is unsubstituted phenyl. In some embodiments, $R^{29}$ is H.

With respect to any relevant formula or structural representation herein, such as Formulas 15-16, in some embodiments, $R^{30}$ may be H, or any substituent, such as $CH_3$, $CH_2CH_3$, or optionally substituted phenyl. In some embodiments, $R^{30}$ is H, or phenyl optionally substituted with F, $CF_3$, $CH_3$, ON, or a combination thereof. In some embodiments, $R^{30}$ is unsubstituted phenyl. In some embodiments, $R^{30}$ is H.

In some embodiments, $R^{27}$ and $R^{28}$ are unsubstituted phenyl. In some embodiments, $R^{27}$, $R^{28}$, and $R^{29}$ are unsubstituted phenyl. In some embodiments, $R^{27}$, $R^{28}$, $R^{29}$, and $R^{30}$ are unsubstituted phenyl.

For convenience, a biphenyl that includes four substituents, such as benzoxazolyl, benzothiazolyl, benzimidazolyl, substituents, including a compound of any of Formulas 1-16, is referred to herein as a "subject compound."

In some embodiments, a subject compound has a highest occupied molecular orbital (HOMO) with an energy of about −6 eV to about −7 eV, about −6 eV to about −6.5 eV, about −6.3 eV to about −6.4 eV, or about −6.35 eV.

In some embodiments, a subject compound has a lowest unoccupied molecular orbital (LUMO) with an energy of about −2 eV to about −3 eV, about −2.5 eV to about −3 eV, about −2.6 eV to about −2.8 eV, or about −2.7 eV.

In some embodiments, a subject compound has an optical band gap of about 3 eV to about 4 eV, about 3.5 eV to about 4 eV, about 3.5 eV to about 3.7 eV, about 3.6 eV to about 3.7 eV, or about 3.65 eV.

In some embodiments, a subject compound has a lowest triplet energy of about 2 eV to about 3 eV, about 2.5 eV to about 3 eV, about 2.5 eV to about 2.7 eV, or about 2.62 eV.

FIG. 1 is a schematic representation of the structure of some embodiments of devices incorporating a subject compound. A light-emitting layer 20 is disposed between a first electrode 2 and a second electrode 4. A nanostructure material 6 is disposed on light-emitting layer 20, and a first charge-transport layer 8 is disposed between the nanostructure material 6 and first electrode 2. An optional second charge-transport layer 9 may be disposed between second electrode 4 and light-emitting layer 20. Other layers, such as charge injection layers (e.g. electron injection layers or hole injection layers), charge blocking layers (e.g. electron blocking layers or hole blocking layers), hole blocking layers, etc., may also be present in the device.

The character of the electrodes and the charge-transport layers may depend upon the particular device structure. For example, if first electrode 2 is an anode, first charge-transport layer 8 is a hole-transport layer, second electrode 4 is a cathode, and second charge-transport layer 9, if present, is an electron-transport layer. Conversely, if first electrode 2 is a cathode, first charge-transport layer 8 is an electron-transport layer, second electrode 4 is an anode, and second charge-transport layer 9, if present, is a hole-transport layer. Thus, a hole-transport layer, if present, may be disposed between a light-emitting layer and an anode, and an electron-transport layer, if present, may be disposed between a light-emitting layer and a cathode.

In addition, the direction of light may depend upon the particular device structure. In some embodiments, the direction of light emitted from the device may depend upon the particular device structure, e.g., top emitting or bottom emitting. In some embodiments, a nanostructure material may be in the path of light emitted from the device. In some embodiments, a nanostructure material may not be in the path of the light emitted from the device. In some embodiments, light 7 can be emitted from the direction of light-emitting layer 20 through the nanostructure material 6, the first charge-transport layer 8, and the first electrode 2. In some embodiments, The path of light emitted by the device may go in the direction away from the nanostructure material 6.

Nanostructure material, e.g. nanostructure material 6, may comprise a substituted biphenyl compound, such as a subject compound, and may be in the form of: a plurality of nanostructures disposed on a surface of the light-emitting layer nearest the first charge-transport layer and/or disposed on a surface of the light-emitting layer distal the first charge-transport layer; and/or in a transitional layer comprising a mixture of the first charge-transport material and the nanostructure material, and disposed between the light-emitting layer and the first charge-transport layer.

Nanostructure material, e.g., nanostructure material 6, may be in the form of a plurality of nanostructures disposed on a surface of or between the light-emitting layer and the hole-transporting layer and/or the electron-transport layer.

Inclusion of nanostructure material may increase luminous efficiency or power efficiency of an OLED by about 10% to about 50% as compared to a similar device without the nanostructure material.

Figure 2A:
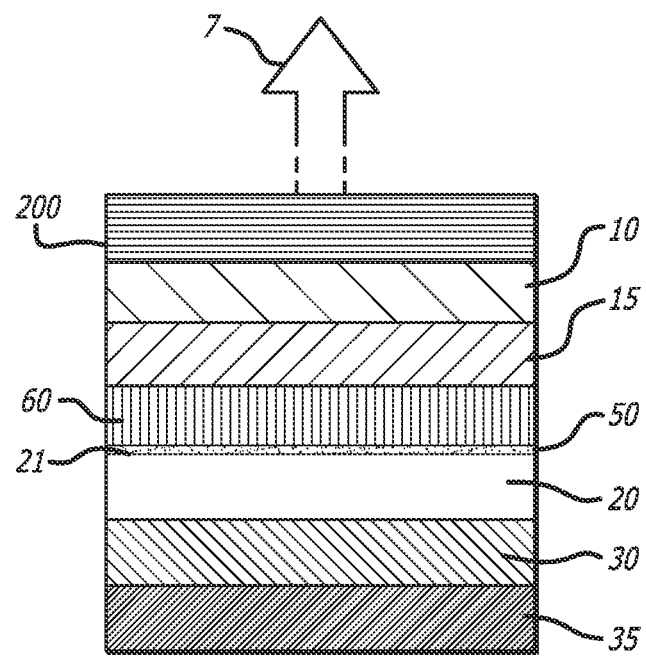
FIG. 2A is a schematic depiction of an embodiment of an organic light-emitting device.
Figure 2B:
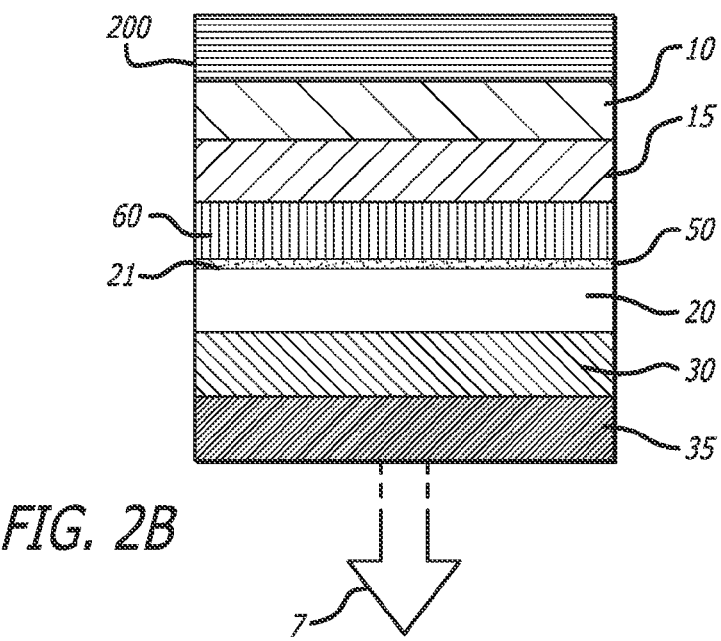
FIG. 2B is a schematic depiction of an embodiment of an organic light-emitting device.

Some embodiments may have a structure represented by FIG. 2A or 2B. A light-emitting layer 20 is disposed between anode 10 and cathode 35. An optional plurality of nanostructures 50 may be disposed on a surface 21 of light-emitting layer 20. An optional transitional layer 60 may be disposed between surface 21 of light-emitting layer 20 and hole-transport layer 15. An optional electron-transport layer 30 may be disposed between light-emitting layer 20 and cathode 35. An optional light-extracting material 200 may be disposed on anode 10. In some embodiments, the anode 10 may be disposed on a transparent substrate (not shown). Other layers may also be present.

In some embodiments, light 7 may be emitted from the direction of light-emitting layer 20 through the plurality of nanostructures 50 (if present), transitional layer 60 (if present), hole-transport layer 15, anode 10, and light-extracting material 200 (if present) (FIG. 2A). In some embodiments, light 7 may be emitted from the direction of the light-emitting layer 20 away from the plurality of nanostructures 50 (if present), through electron-transport of layer 30 (if present) and through cathode 35 (FIG. 2B).

Figure 3A:
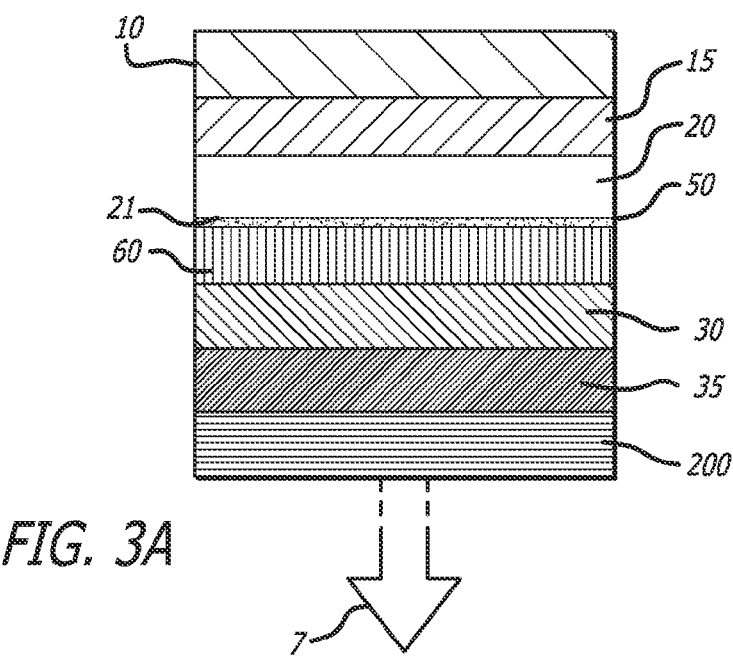
FIG. 3A is a schematic depiction of an embodiment of an organic light-emitting device.
Figure 3B:
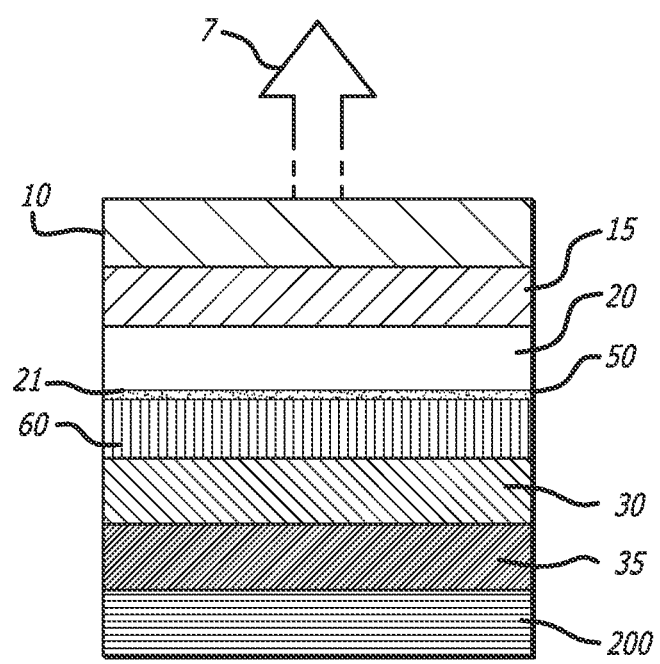
FIG. 3B is a schematic depiction of an embodiment of an organic light-emitting device.

Some embodiments may have a structure represented by FIG. 3A or 3B. A light-emitting layer 20 is disposed between an anode 10 and a cathode 35. An electron-transport layer 30 is disposed between light-emitting layer 20 and cathode 35. An optional plurality of nanostructures 50 may be disposed on a surface 21 of light-emitting layer 20. An optional transitional layer 60 may be disposed between surface 21 of light-emitting layer 20 and electron-transport layer 30. An optional hole-transport layer 15 may be disposed between anode 10 and light-emitting layer 20. Cathode 35 may be disposed on optional light-extracting material 200. Light 7 may be emitted from the direction of light-emitting layer 20 through the plurality of nanostructures 50 (if present), transitional layer 60 (if present), electron-transport layer 30, cathode 35, and light-extracting material 200 (if present). Other layers may also be present (FIG. 3A). In some embodiments, light 7 may be emitted in the direction away from plurality of nanostructures 50 through hole-transport layer 15 (if present), and through anode 10 (FIG. 3B).

A plurality of nanostructures, e.g. nanostructures 50, can comprise a subject compound, and may form a rough interface with the next layer, e.g. a transitional layer or a charge-transport layer. In some embodiments, the plurality of nanostructures 50 have an irregular periodicity within in the matrix material. In some embodiments, the periodicity of the nanostructures in the interface or surface of the nanostructured layer is between about 0.00001 um to about 50 um. In some embodiments, the periodicity may be between about 0.0001 μm and about 1.0 μm. In some embodiments, the periodicity may be between about 0.1 μm and about 10.0 μm.

In some embodiments, the area of the individual nanostructures as projected within the x,y plane or surface 21 can be within about 0.0001 $\mu m^2$ to about 1.0 $\mu m^2$. In some embodiments the area of the individual nanostructures as projected within the x,y plane can be between about 1 $\mu m^2$ to about 3 $\mu m^2$. In some embodiments, the area of the individual nanostructures as projected within the x,y plane can be between about 0.04 $\mu m^2$ to about 0.150 $\mu m^2$.

In some embodiments, a plurality of nanostructures disposed on a surface of a light-emitting layer may have a total mass of about 1 ng to about 500 ng, about 10 ng to about 100 ng, or about 20 ng to about 60 ng for each $cm^2$ of area of the surface of the light-emitting layer.

In some embodiments, the nominal thickness of a plurality of nanostructures measured by the Quartz Crystal microbalance, which measures the mass deposited onto it, is about 0.0001 nm to about 50 nm or about 0.001 nm to about 10 nm. In some embodiments, the light extraction layer is a discontinuous layer including apertures or voids between islands of light extraction material.

In some embodiments, a plurality of nanostructures thereof may be substantially transparent or substantially translucent.

A plurality of nanostructures may be deposited by vacuum evaporation and can self-assemble into various types of nanostructures described above, depending on the deposition rate. The size and distribution of nanostructures may depend on the deposition rate of the materials. For example, nanostructures may become smaller in all dimensions with increasing deposition rate. In some embodiments, the deposition rate may be about 0.005 nm/s to about 500 nm/s, about 0.005 nm/s, about 0.01 nm/s, about 0.02 nm/s, about 0.03 nm/s, about 0.05 nm/s, about 0.08 nm/s, about 0.1 nm/s, about 0.2 nm/s, about 0.5 nm/s, about 1 nm/s, about 10 nm/s, about 100 nm/s, or any value in a range bounded by, or between, any of these deposition rates. In some embodiments, output enhancement, e.g. the amount of light extracted from the device, may increase with the deposition rate. In some embodiments, output enhancement, e.g. the amount of light extracted from the device, may increase with the deposition rate being between about 0.01 A/s to about 1.5 A/s.

In some embodiments, the area of the nanostructure material disposed within or upon substrate surface, e.g., the light-emitting layer, may vary. In an embodiment, the area of the particles may range between about 0.0001 $\mu m^2$ to about 1.0 $\mu m^2$. In an embodiment, the area of the particles may range between about 0.001 $\mu m^2$ to about 0.5 $\mu m^2$.

In some embodiments, the periodicity (separation) of the nanostructure material within or upon the deposed surface, e.g., the light-emitting layer, may vary. In some embodiments, the period of the particles may range between about 0.001 μm to about 20 μm. In some embodiments, the period of the particles may range between about 0.050 μm to about 5 μm.

An anode, e.g. anode 10, may be a layer comprising a conventional material such as a metal, a mixed metal, an alloy, a metal oxide or a mixed-metal oxide, a conductive polymer, and/or an inorganic material such as a carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. If the anode layer is to be light-transmitting, e.g., bottom emitting light-emitting diode construction, the anode layer may include a transparent substrate upon which the light-emitting material is disposed. Suitable transparent materials include, but are not limited to, glass, transparent polymers and transparent plastics. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). In some embodiments, the anode layer can have a thickness in the range of about 1 nm to about 1000 nm.

layer to lower the operating voltage. Suitable low work function metals include but are not limited to Al, Ag, Mg, Ca, Cu, Mg/Ag, LiF/Al, CsF, CsF/Al, ITO, IZO or alloys thereof. In some embodiments, the cathode layer can have a thickness in the range of about 1 nm to about 1000 nm.

A light-emitting layer, e.g. light-emitting layer 20, may comprise a light-emitting component and a host. Suitable host materials include, but are not limited to those described in co-pending patent applications, U.S. Patent Publication 2011/0140093 (Ser. No. 13/033,473, filed 23 Feb. 2011). In some embodiments, the host may be any of:

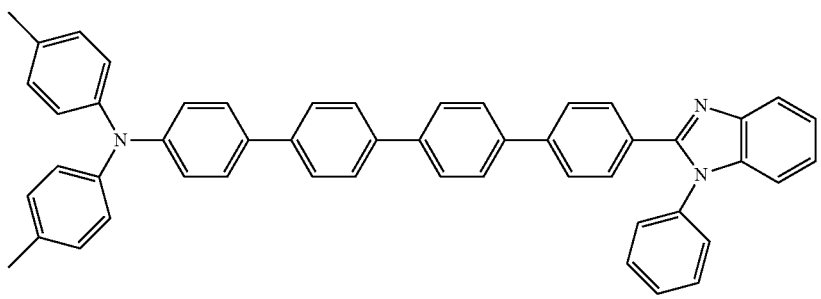

4'''-(1-phenyl-1H-benzo[d]imidazol-2-yl)-N,N-di-p-tolyl-[1,1':4',1":4", 1'''-quaterphenyl]-
4-
amine (Host-1)

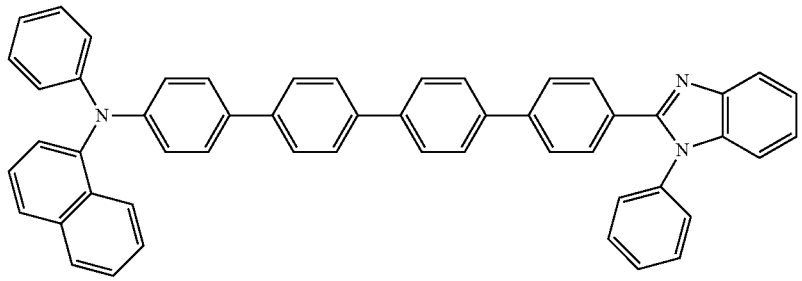 [SMILES: c1ccc(N(c2ccc(-c3ccc(-c4ccc(-c5ccc(-c6nc7ccccc7n6-c6ccccc6)cc5)cc4)cc3)cc2)c2cccc3ccccc23)cc1]

9-(4'''-(1-phenyl-1H-benzo[d]imidazol-2-yl)-[1,1':4',1":4", 1'''-quaterphenyl]-4-yl)-9H-
carbazole (Host-2)

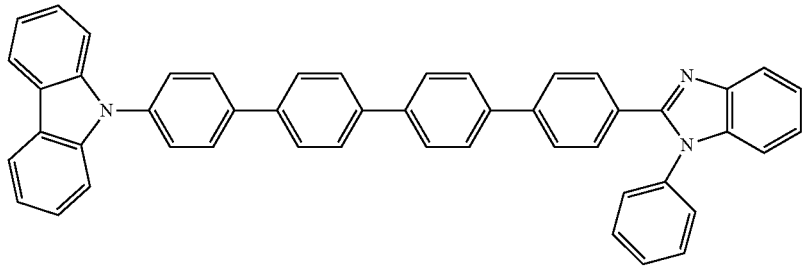

9-(4'''-(1-phenyl-1H-benzo[d]imidazol-2-yl)-[1,1':4',1":4", 1'''-quaterphenyl]-4-yl)-9H-
carbazole (Host-2)

A cathode, e.g. cathode 35, may be a layer including a material having a lower work function than the anode layer. Examples of suitable materials for the cathode layer include mixed-metal oxides of Group 12, 13, and 14 metals, such as indium-tin-oxide (ITO), indium-zinc-oxide (IZO), alkali metals of Group 1, Group 2 metals, Group 12 metals, including rare earth elements, lanthanides and actinides, materials such as aluminum, indium, calcium, barium, samarium and magnesium, and combinations thereof. Li-containing organometallic compounds, LiF, and Li$_2$O may also be deposited between the organic layer and the cathode The amount of the host in a light-emitting layer may vary. In some embodiments, the amount of a host in a light-emitting layer is in the range of from about 70% to nearly 100% by weight of the light-emitting layer, such as about 90% to about 99%, or about 97% by weight of the light-emitting layer. In some embodiments, the mass of the light-emitting component is about 0.1% to about 10%, about 1% to about 5%, or about 3% of the mass of the light-emitting layer. The light-emitting component may be a fluorescent and/or a phosphorescent compound.

A light-emitting component may comprise an iridium coordination compound such as: bis-{2-[3,5-bis(trifluoromethyl)phenyl]pyridinato-N,C2'}iridium(III)-picolinate; bis (2-[4,6-difluorophenyl]pyridinato-N,C2')iridium (III) picolinate; bis(2-[4,6-difluorophenyl]pyridinato-N,C2')iridium (acetylacetonate); Iridium (III) bis(4,6-difluorophenylpyridinato)-3-(trifluoromethyl)-5-(pyridine-2-yl)-1,2,4-triazolate; Iridium (III) bis(4,6-difluorophenylpyridinato)-5-(pyridine-2-yl)-1H-tetrazolate; bis[2-(4,6-difluorophenyl)pyridinato-N,C2']iridium(III)tetra (1-pyrazolyl)borate; bis[2-(2'-benzothienyl)-pyridinato-N,C3']iridium (III)(acetylacetonate); bis[(2-phenylquinolyl)-N,C2']iridium (III) (acetylacetonate); bis[(1-phenylisoquinolinato-N,C2')]iridium (III) (acetylacetonate); bisRdibenzo[f,h]quinoxalino-N,C2')iridium (III)(acetylacetonate); tris(2,5-bis-2'-(9',9'-dihexylfluorene)pyridine) iridium (III); tris[1-phenylisoquinolinato-N,C2']iridium (III); tris-[2-(2'-benzothienyl)-pyridinato-N,C3'] iridium (III); tris[1-thiophen-2-ylisoquinolinato-N,C3']iridium (III); tris[1-(9,9-dimethyl-9H-fluoren-2-yl)isoquinolinato-(N,C3')iridium (III)); bis(2-phenylpyridinato-N,C2')iridium (III)(acetylacetonate) [Ir(ppy)₂(acac)]; bis(2-(4-tolyl)pyridinato-N,C2')iridium(III)(acetylacetonate) [Ir(mppy)₂(acac)]; bis(2-(4-tert-butyl)pyridinato-N,C2')iridium (III)(acetylacetonate) [Ir(t-Buppy)₂(acac)]; tris(2-phenylpyridinato-N,C2')iridium (III) [Ir(ppy)₃]; bis(2-phenyloxazolinato-N,C2') iridium (III) (acetylacetonate) [Ir(op)₂(acac)]; tris(2-(4-tolyl)pyridinato-N,C2')iridium(III) [Ir(mppy)₃]; bis[2-phenylbenzothiazolato-N,C2'] iridium (III) (acetylacetonate); bis[2-(4-tert-butylphenyl) benzothiazolato-N,C2']iridium(III)(acetylacetonate); bis[(2-(2'-thienyl)pyridinato-N,C3')]iridium (III) (acetylacetonate); tris[2-(9.9-dimethylfluoren-2-yl)pyridinato-(N,C3')]iridium (III); tris[2-(9.9-dimethylfluoren-2-yl)pyridinato-(N,C3')] iridium (III); bis[5-trifluoromethyl-2-[3-(N-phenylcarbzolyl)pyridinato-N,C2']iridium(III)(acetylacetonate); (2-PhPyCz)₂Ir(III)(acac); etc.

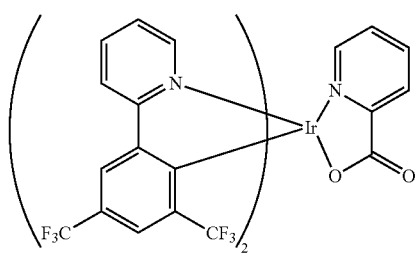

bis-{2-[3,5-bis(trifluoromethyl)phenyl]pyridinato-N,C2'}iridium(III)-picolinate(Ir(CF₃ppy)₂(Pic)

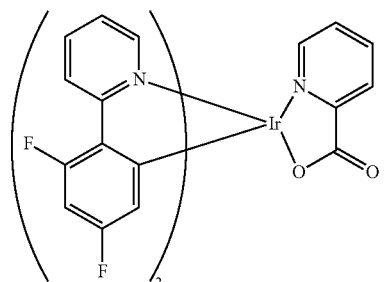

bis(2-[4,6-difluorophenyl]pyridinato-N,C2')iridium (III) picolinate [FIrPic]

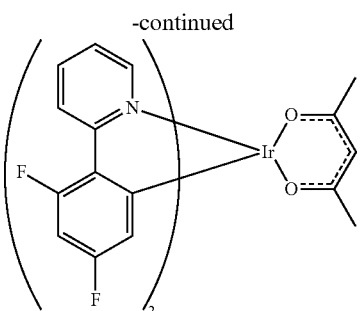

bis(2-[4,6-difluorophenyl]pyridinato-N,C2')iridium(acetylacetonate) [FIr(acac)]

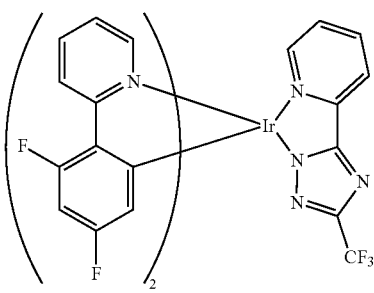

Iridium (III) bis(4,6-difluorophenylpyridinato)-3-(trifluoromethyl)-5-(pyridine-2-yl)-1,2,4-triazolate (FIrtaz)

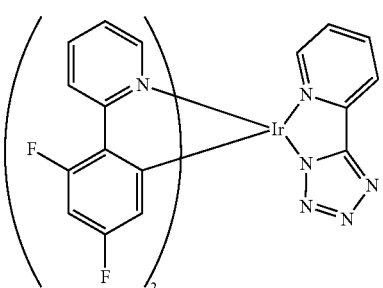

Iridium (III) bis(4,6-difluorophenylpyridinato)-5-(pyridine-2-yl)-1H-tetrazolate (FIrN4)

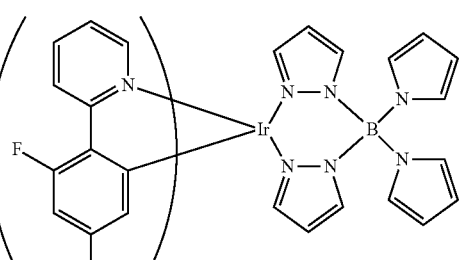

bis[2-(4,6-difluorophenyl)pyridinato-N,C2']iridium(III)tetra(1-pyrazolyl)borate (Fir6)

-continued
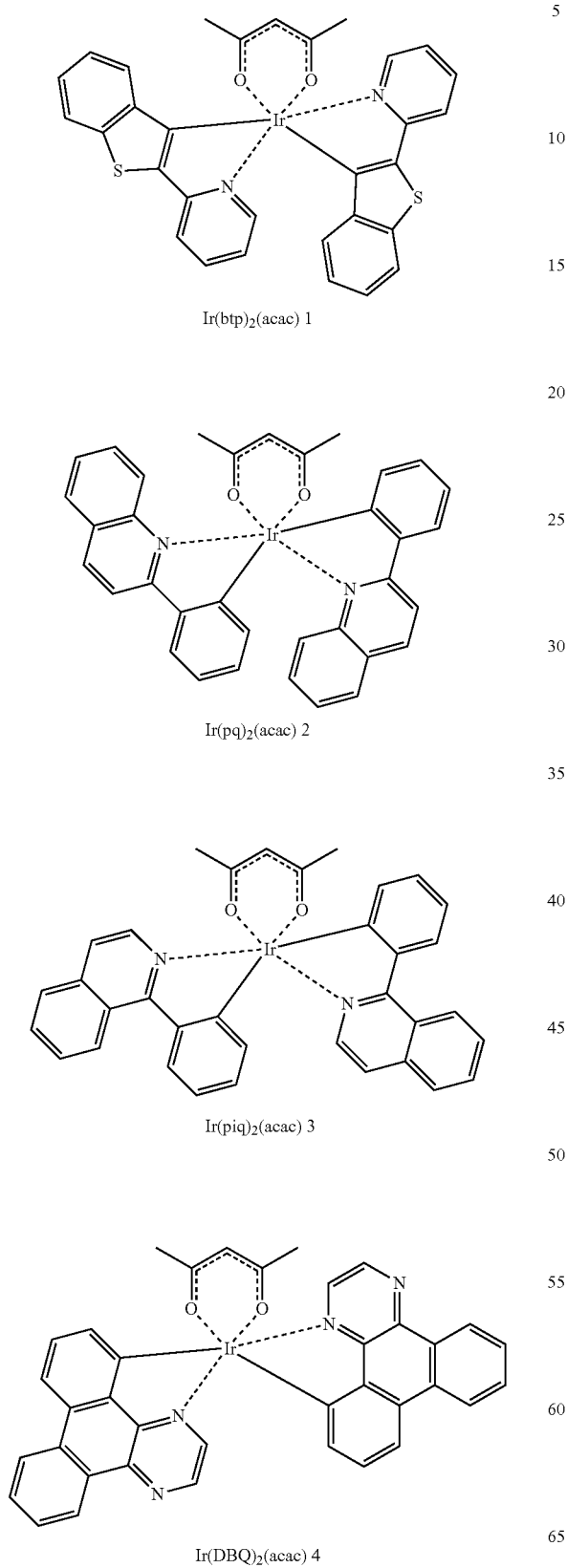
Ir(btp)₂(acac) 1
Ir(pq)₂(acac) 2
Ir(piq)₂(acac) 3
Ir(DBQ)₂(acac) 4
-continued
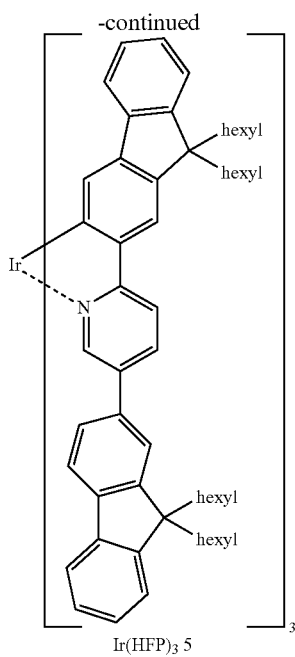
Ir(HFP)₃ 5
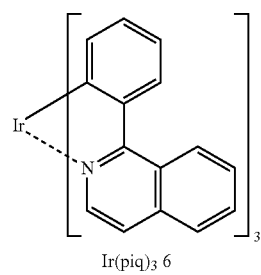
Ir(piq)₃ 6
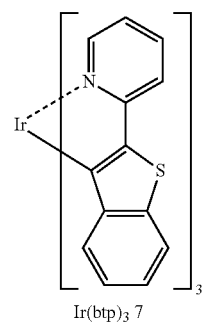
Ir(btp)₃ 7
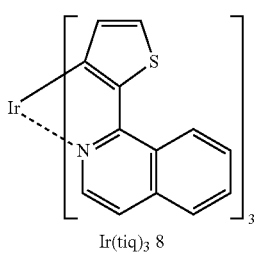
Ir(tiq)₃ 8

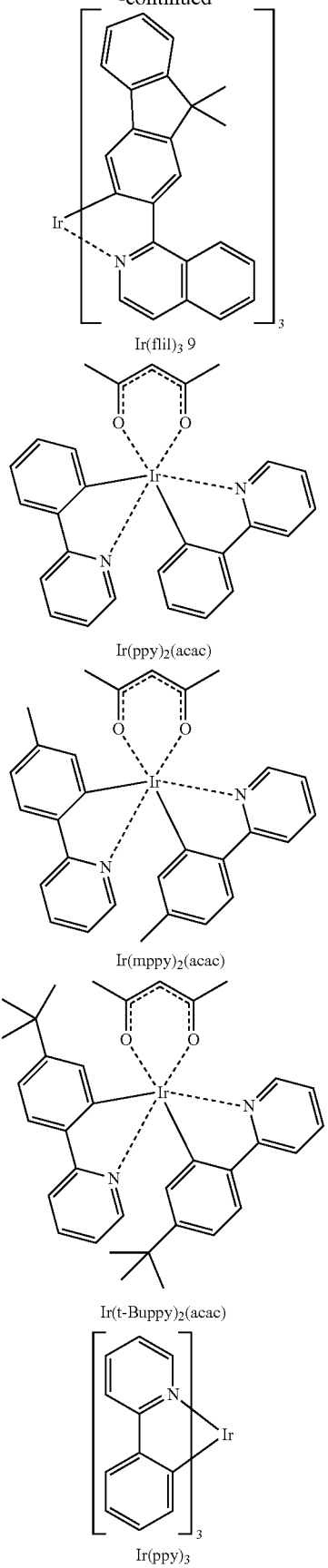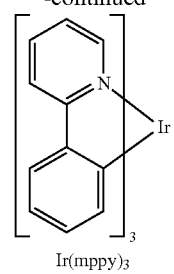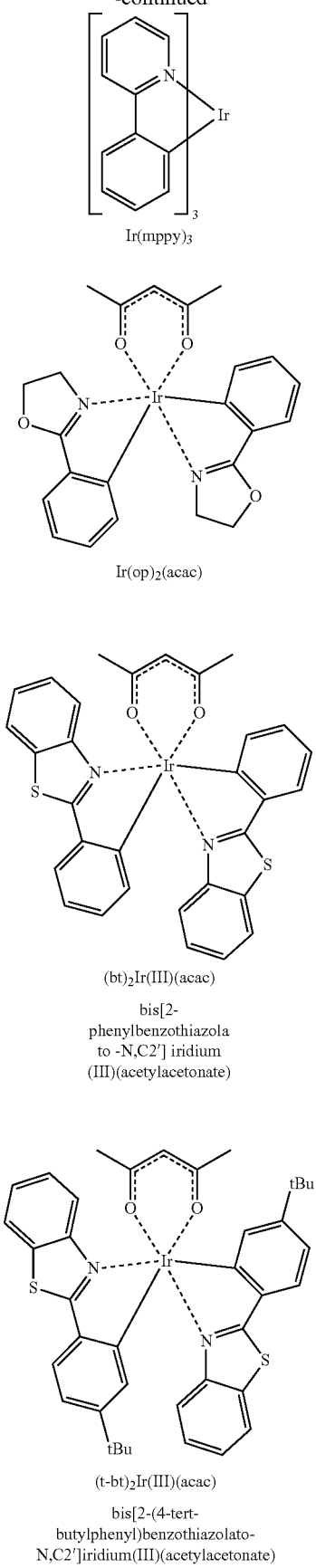

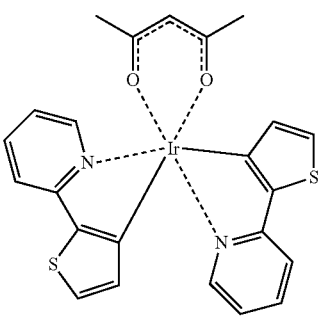

(thp)₂Ir(III)(acac)
bis[(2-(2'-thienyl)pyridinato-N,C3']iridium(III)(acetylacetonate)

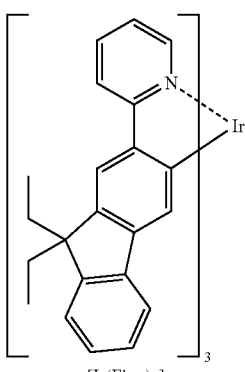

[Ir(Flpy)₃]

tris[2-(9,9-dimethylfluoren-2-yl)pyridinato-(N,C3')]iridium (III)

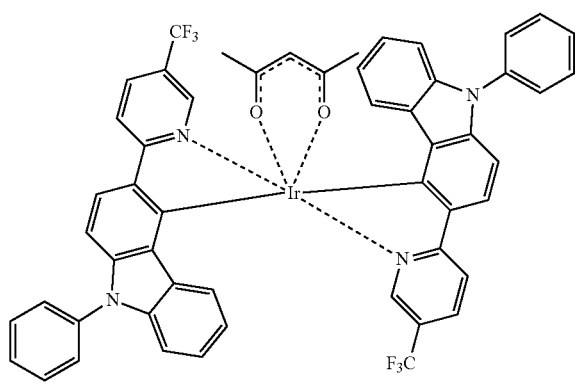

(Cz-CF₃)Ir(III)(acac)

Bis[5-trifluoromethyl-2-[3-(N-phenylcarbzolyl)pyridinato-N,C2']iridium(III)(acetylacetonate)

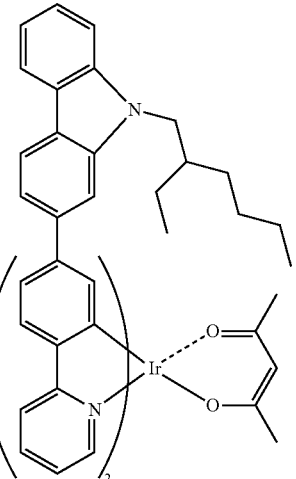

(2-PhPyCz)₂Ir(III)(acac)

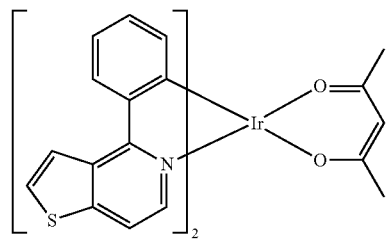

YE-1

1. (Btp)₂Ir(III)(acac); bis[2-(2'-benzothienyl)-pyridinato-N,C3'] iridium (III)(acetylacetonate)
2. (Pq)₂Ir(III)(acac); bis[2-phenylquinolyl)-N,C2']iridium (III) (acetylacetonate)
3. (Piq)₂Ir(III)(acac); bis[(1-phenylisoquinolinato-N,C2')iridium (III) (acetylacetonate
4. (DBQ)₂Ir(acac); bis[(dibenzo[f, h]quinoxalino-N,C2')iridium (III)(acetylacetonate)
5. [Ir(HFP)₃], tris(2,5-bis-2'-(9',9'-dihexylfluorene)pyridine)iridium (III)
6. Ir(piq)₃; tris[1-phenylisoquinolinato-N,C2']iridium (III)
7. Ir(btp)₃; tris[2-(2'-benzothienyl)-pyridinato-N,C3'] iridium (III)
8. Ir(tiq)₃; tris[1-thiophen-2-ylisoquinolinato-N,C3']iridium (III)
9. Ir(fliq)₃; tris[1-(9,9-dimethyl-9H-flouren-2-yl)isoquinolinato-(N,C3')iridium (III)

The thickness of a light-emitting layer may vary. In one embodiment, a light-emitting layer has a thickness in the range of from about 1 nm to about 200 nm, 5 nm to about 150 nm, about 10 nm to about 50 nm, or about 20 nm or about 30 nm.

An optional transitional layer may comprise a mixture of nanostructure material and charge-transport material, such as a hole-transport material or an electron-transport material. Generally, the character of the charge-transport material in the transitional layer depends upon the position of the transitional layer. For example, a transitional layer disposed between a light-emitting layer and a hole-transport layer may comprise a mixture of a hole-transport material and a nanostructure material; and/or a transitional layer disposed between a light-emitting layer and an electron-transport layer may comprise a mixture of an electron-transport material and a nanostructure material. A nanostructure material may have charge-transport properties similar to those of the material with which it is mixed. For example, a nanostructure material with hole-transport properties may be mixed with a hole-transport material in a transitional layer; and/or a nanostructure material with electron-transport properties may be mixed with an electron-transport material in a transitional layer.

The thickness of a transitional layer may vary. In some embodiments, a transitional layer may have a thickness of about 1 nm to about 50 nm, about 5 nm to about 30 nm, or about 8 nm to about 15 nm. In some embodiments, a transition layer is not present.

In a transitional layer, the weight ratio of nanostructure material to charge-transport material may vary, such as about 10:1 to about 1:10, about 1.2:1 to about 1:1.2, or 1:1 to about 1:10, or any ratio in a range bounded by, or between, any of these values.

If present, a hole-transport layer, e.g. hole-transport layer 15, may be disposed between the anode and the light-emitting layer. A hole-transport layer may comprise at least one hole-transport material. Hole-transport materials may include, but are not limited to, an aromatic-substituted amine, a carbazole, a polyvinylcarbazole (PVK), e.g. poly (9-vinylcarbazole); polyfluorene; a polyfluorene copolymer; poly(9,9-di-n-octylfluorene-alt-benzothiadiazole); poly (paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-bis(4-bis(4-methylphenyl)aminophenyl)cyclohexane; 2,9-dimethyl-4,7-diphenyl-1,10-phenanthroline; 3,5-bis(4-tert-butyl-phenyl)-4-phenyl[1,2,4]triazole; 3,4,5-triphenyl-1,2,3-triazole; 4,4',4'-tris(3-methylphenylphenylamino) triphenylamine (MTDATA); N,N'-bis(3-methylphenyl)N, N'-diphenyl-[1,1'-biphenyl]-4,4'-diamine (TPD); 4,4'-bis[N-(naphthyl)-N-phenyl-amino]biphenyl (α-NPD); 4,4',4''-tris (carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); bis[4-(p,p'-ditolyl-amino)phenyl]diphenylsilane (DTASi); 2,2'-bis(4-carbazolylphenyl)-1,1'-biphenyl (4Cz-PBP); N,N'N''-1,3,5-tricarbazoloylbenzene (tCP); N,N'-bis (4-butylphenyl)-N,N'-bis(phenyl)benzidine; N,N'-Di(naph-thalene-1-yl)-N,N'-diphenyl-benzidine (NPB) or the like.

If present, an electron-transport layer, e.g. electron-transport layer 30, may be disposed between the cathode and the light-emitting layer. Examples of electron-transport materials may include, but are not limited to, 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyri-dine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]ben-zene (TPBI). In one embodiment, the electron-transport layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl] benzene (TPBI), or a derivative or a combination thereof.

The thickness of an electron-transport layer may vary. For example, some electron-transport layers may have a thickness of about 5 nm to about 200 nm, about 10 nm to about 80 nm, or about 20 nm to about 40 nm.

If desired, additional layers may be included in a light-emitting device, such as an electron injecting layer (EIL), a hole-blocking layer (HBL), an exciton-blocking layer (EBL), a hole-injecting layer (HIL), etc. In addition to separate layers, some of these materials may be combined into a single layer.

If present, an electron-injecting layer may be between a cathode layer and a light-emitting layer. Examples of suitable material(s) that can be included in the electron injecting layer include but are not limited to, an optionally substituted compound selected from the following: aluminum quinolate (Alq$_3$), 2-(4-biphenylyl)-5-(4-tert-butylphenyl)-1,3,4-oxadi-azole (PBD), phenanthroline, quinoxaline, 1,3,5-tris[N-phe-nylbenzimidazol-z-yl]benzene (TPBI) a triazine, a metal chelate of 8-hydroxyquinoline such as tris(8-hydroxyquino-liate) aluminum, and a metal thioxinoid compound such as bis(8-quinolinethiolato) zinc. In one embodiment, the elec-tron injecting layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimida-zol-z-yl] benzene (TPBI), or a derivative or a combination thereof.

If present, a hole-blocking layer may be between a cathode and a light-emitting layer. Examples of suitable hole-blocking material(s) include but are not limited to, an optionally substituted compound selected from the follow-ing: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, a light-emitting device can include an exciton-blocking layer. In an embodiment, the band gap of the material(s) that comprise exciton-blocking layer is large enough to substantially prevent the diffusion of exci-tons. A number of suitable exciton-blocking materials that can be included in the exciton-blocking layer are known to those skilled in the art. Examples of material(s) that can compose an exciton-blocking layer include an optionally substituted compound selected from the following: alumi-num quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

If present, a hole-injecting layer may be between the light-emitting layer and the anode. Examples of suitable hole-injecting material(s) include, but are not limited to, an optionally substituted compound selected from the follow-ing: a polythiophene derivative such as poly(3,4-ethylene-dioxythiophene (PEDOT)/polystyrene sulphonic acid (PSS), a benzidine derivative such as N,N,N',N'-tetraphenylbenzi-dine, poly(N,N'-bis(4-butylphenyl)-N,N'-bis(phenyl)benzi-dine), a triphenylamine or phenylenediamine derivative such as N,N'-bis(4-methylphenyl)-N,H-bis(phenyl)-1,4-phe-nylenediamine, 4,4',4''-tris(N-(naphthylen-2-yl)-N-phe-nylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper.

If present, in some embodiments, the light extraction material 200 may comprise a substituted biphenyl com-pound, such as a subject compound, and may be a light extraction film. The light-extracting material 200 may be disposed on: the anode, the cathode, a transparent layer disposed between the anode and the light extraction mate-rial, and/or a transparent layer disposed between the cathode and the light extraction material. A light extraction material may comprise any nanostructure material described above, and may comprise any nanostructure as described above, as well as nanostructures or microstructures of a larger size. For example, nanostructures may have: an averagexdimen-sion of about 400 nm, about 500 nm, about 1000 nm, about 1500 nm, about 2000 nm, about 2500 nm, about 3000 nm, or any value in a range bounded by, or between, any of these lengths; an average y dimension of about 50 nm, about 100 nm, about 300 nm, about 500 nm, about 700 nm, about 1000 nm, about 1200 nm, about 1500 nm, about 1800 nm, about 2000 nm, or any value in a range bounded by, or between, any of these lengths; and/or an average z dimension of about 10 nm, about 30 nm, about 50 nm, about 70 nm, about 90 nm, about 100 nm, or any value in a range bounded by, or between, any of these lengths. In some embodiments, at least one particle in the film, or average of the particles in the film, may have an x dimension, a y dimension, or a z dimension of: about 5 nm, about 0.01 µm, about 0.02 µm, about 0.05 µm, about 0.1 µm, about 0.5 µm, about 1 µm, about 2 µm, about 5 µm, about 10 µm, about 20 µm, about 50 µm, about 100 µm, about 150 µm, about 200 µm, about 500 µm, about 1000 µm, or any length bounded by, or between, any of these values.

In some embodiments, the light extraction material 200 may comprise a regular, quasi-regular, or random nanostructures formed within or on the surface of the light extraction layer or as a separate optional layer of material having such nanostructures formed within a surface of such layer. Suitable examples, include, but are not limited to, prismatic surfaced layers as described in U.S. Pat. Nos. 7,957,621; 7,799,416; 6,707,611; and 6,354,709, which are incorporated by reference herein for their description of brightness enhancing films, e.g., those sold under the brand name Vikuti by 3M (Minneapolis, Minn.). Another suitable example are light extraction materials include layers comprising a transparent or translucent material having a periodic pattern formed on the surface thereof. One suitable example is the microlens array (MLA) of periodic or repeating pattern of spherical or trapezoidal shapes formed within a surface of a transparent or translucent material. Suitable examples include, but are not limited to U.S. Pat. Nos. 6,594,079 and 7,864,450, which are incorporated by reference herein for their description of microlens arrays or bubble array layers.

The thickness of a light-extracting material may vary. In some embodiments, a light-extracting material may have a thickness in the nanometer to micron range. For example, the thickness of the film may be about 500 nm, about 0.1 µm, about 1 µm, about 1.3 µm, about 3 µm, or about 4 µm, about 5 µm, about 7 µm, about 10 µm, about 20 µm, about 100 µm, or any thickness in a range bounded by, or between, any of these values.

A light-extracting layer may comprise a number of pores or voids. For example, a light-extracting layer may comprises a plurality of voids having a total volume that may be about 50%, about 70%, about 80%; about 85%, about 90%, about 95%, or about 99% of the volume of the film, or any percentage of total volume in a range bounded by, or between, any of these values.

In some embodiments, a layer of a light-extracting material may comprises a plurality of voids of a number and size such that the layer may have a thickness that is about 2 times, about 10 times, up to about 50 times, or 100 times, that of the thickness of a layer of the same material which has no voids, or any thickness ratio in a range bounded by, or between, any of these values. For example, a film may have a thickness of about 5 µm when a film of the same material would have a thickness of 800 nm if the film had no voids.

The size of the voids may vary. The dimensions of a void may be quantified in a manner analogous to that described above for a nanostructure. In some embodiments, at least about 10% of the voids have a largest dimension, or an x dimension, of about 0.5 µm, about 1 µm, about 2 µm, about 3 µm, about 4 µm, about 5 µm, or any length in a range bounded by, or between, any of these values. In some embodiments, at least one void in the film, or average of the voids in the film, may have an x dimension, a y dimension, or a z dimension of: about 5 nm, about 0.01 µm, about 0.02 µm, about 0.05 µm, about 0.1 µm, about 0.5 µm, about 1 µm, about 2 µm, about 5 µm, about 10 µm, about 20 µm, about 50 µm, about 100 µm, about 150 µm, about 200 µm, about 500 µm, about 1000 µm, or any length bounded by, or between, any of these values.

The density of light-extracting materials may vary, and may be affected by the voids, the material, and other factors. In some embodiments, the density of a layer of light-extracting material including the voids may be about 0.005 picograms/µm$^3$, about 0.05 picograms/µm$^3$, about 0.1 picograms/µm$^3$, about 0.3 picograms/µm$^3$, 0.5 picograms/µm$^3$, about 0.7 picograms/µm$^3$, about 0.9 picograms/µm$^3$, or any density in a range bounded by, or between, any of these values.

The refractive index of the light-extracting material may vary. For example, the refractive index may be about 1.1, about 1.5, about 1.7, about 1.8, or any refractive index in a range bounded by, or between, any of these values. In some embodiments, the refractive index of the material of the light-extracting layer may be greater than or equal to that of the substrate.

In some embodiments, the combination of a light-extracting layer and a nanostructure material in an OLED may increase the light output by about 70% or more. In some embodiments, the combination of a light-extracting layer and a nanostructure material dispersion in an OLED may increase the light output more than the summed increase light output of an OLED with only an extraction layer and one with only nanostructures. Light-emitting devices comprising a subject compound can be fabricated using techniques known in the art, as informed by the guidance provided herein. For example, a glass substrate can be coated with a high work functioning metal such as ITO which can act as an anode. After patterning the anode layer, a hole-injecting and/or hole-transport layer may be deposited on the anode in that order. A light-emitting layer that includes a light-emitting component, can be deposited on the anode, the hole-transport layer, or the hole-injecting layer. An electron-transport layer and/or an electron-injecting layer may deposited in that order on the light-emitting component. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

EXAMPLE

Example 1

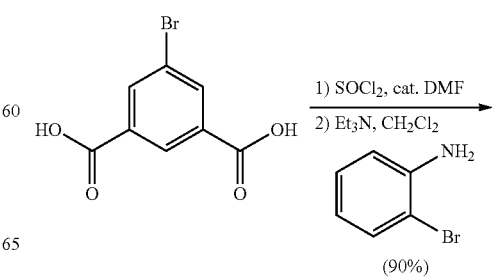

-continued

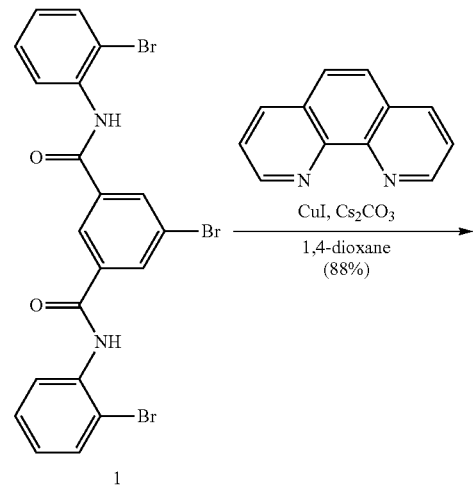

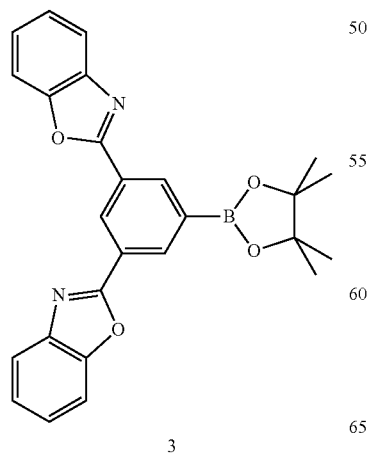

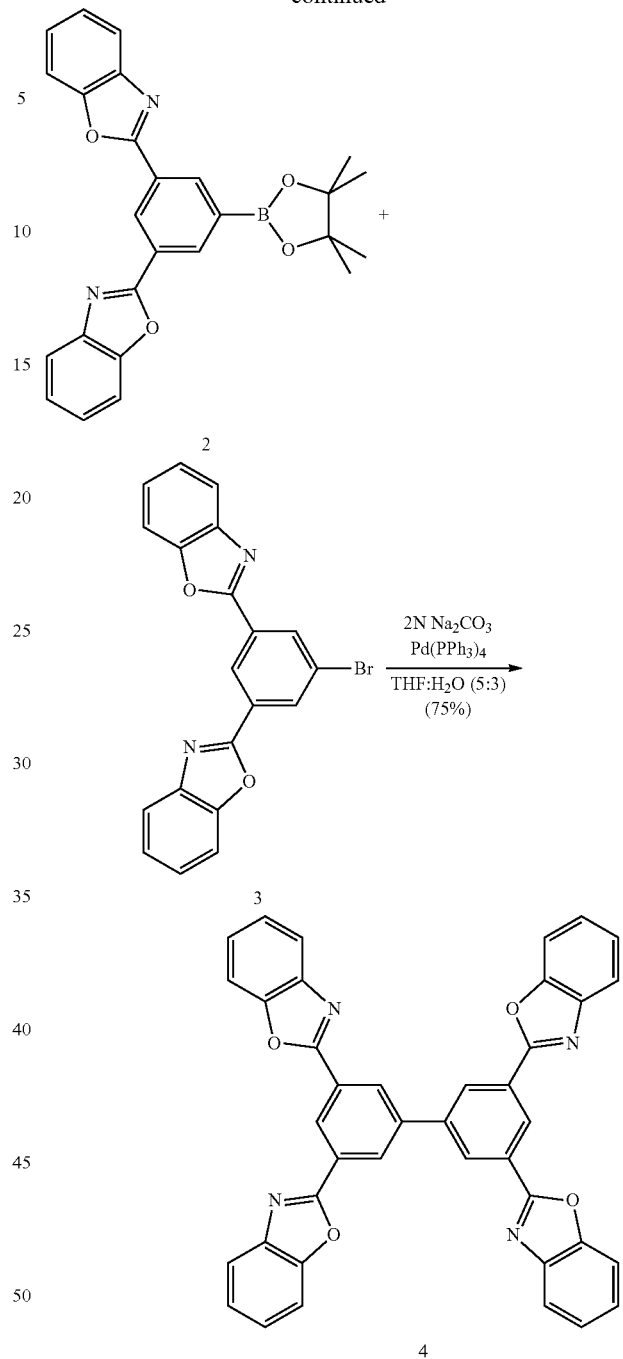

5-bromo-$N^1$,$N^3$-bis(2-bromophenyl)isophthalamide (1)

A mixture of 5-bromoisophtalic acid (10.00 g, 40.81 mmol) and cat. DMF (5 drops) in thionyl chloride (40 mL, 551 mmol) was heated to reflux under Ar overnight. After removal of the excess thionyl chloride under vacuum, the crude intermediate was dissolved in anhydrous $CH_2Cl_2$ (200 mL). To the chilled (0° C.) solution was added 2-bromoaniline (14.04 g, 81.62 mmol), followed by dropwise addition of triethylamine (15 mL). The mixture was then stirred overnight and allowed to warm to room temperature (RT).

The resulting suspension was filtered and washed with CH$_2$Cl$_2$ to afford crude 1 (20.3 g, 90%) as an off-white solid:

2,2'-(5-bromo-1,3-phenylene)bis(benzo[d]oxazole) (2)

A mixture of 1 (20.3 g, 36.7 mmol), CuI (0.700 g, 3.67 mmol), Cs$_2$CO$_3$ (23.9 g, 73.5 mmol), 1,10-phenanthroline (1.32 g, 7.35 mmol) and 1,4-dioxane (300 mL) was degassed with Ar and then maintained at 120° C. overnight. Upon confirming consumption of the starting material by TLC (SiO$_2$, 4:1 hexanes-ethyl acetate), the reaction was cooled to RT and diluted with EtOAc (ca. 300 mL) and H$_2$O (ca. 400 mL). The resulting suspension was then filtered and the filtrate washed copiously with H$_2$O and CH$_3$OH to provide 2 (12.7 g, 88%) as an off-white solid:

2,2'-(5-(4,4,5,5-tetramethyl-1,3,2-dioxaborolan-2-yl)-1,3-phenylene)bis(benzo[d]oxazole) (3)

A mixture of 2 (10.0 g, 25.6 mmol), bis(pinacolato)diboron (7.14 g, 28.1 mmol), [1,1'-bis(diphenylphosphino)ferrocene]dichloropalladium(II) (0.935 g, 1.28 mmol), potassium acetate (7.53 g, 76.7 mmol) and 1,4-dioxane (125 mL) was degassed with argon and then maintained under argon at 80° C. while stirring. Upon confirming consumption of the starting material by TLC (SiO$_2$, 4:1 hexanes-ethyl acetate), the reaction was cooled to RT and poured over EtOAc and brine. The mixture was then filtered and the filtrant washed copiously with H$_2$O to afford 3 (10.2 g, 91%) as a grey solid:

3,3',5,5'-tetrakis(benzo[d]oxazol-2-yl)-1,1'-biphenyl (4)

A mixture of compound 2 (1.26 g, 3.21 mmol), compound 3 (1.48 g, 3.37 mmol), tetrakis(triphenylphosphine)palladium(0) (0.223 g, 0.190 mmol), Na$_2$CO$_3$ (3.92 g, 36.9 mmol), H$_2$O (37 mL) and THF (62 mL) was degassed with argon for 15 min while stirring. The reaction mixture was then maintained under argon at 85° C. for 66 h. Upon cooling to RT, the reaction mixture was filtered and the filtrant washed copiously with H$_2$O and CH$_3$OH to provide 4 (1.96 g, 98%) as an off-white solid:

FIG. 4 depicts the structure of a devise that may be prepared as follows: ITO anode 520 coated (110 nm) glass substrate 510 is cleaned by ultrasound in detergent, deionized water, acetone, and 2-propanol consecutively, then baked at 110° C. for 3 hours, followed by treatment with oxygen plasma for 30 min. A hole-injecting layer 530 of PEDOT: PSS (HIL 1.1 from N.C. Starck) is spin-coated at 4000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of 10$^{-7}$ torr, a hole-transport layer 540 of NPB is first deposited on top of PEDOT/PSS layer at deposition rate of 0.1 nm/s, yielding a 30 nm thick film. A 20 nm-thick light-emitting 550 layer of Host-2 doped with 10 wt % red phosphorescent emitter Ir(piq)$_2$acac is deposited on top of hole-transport layer 540. Afterwards a 0.4 nm-thick deposit of a plurality of nanostructures 560 (measured by the Quartz sensor) of TBB is deposited at deposition rate around 0.01 nm/s. Then a 40 nm-thick electron-transport layer 580 of TPBi is deposited at 0.1 nm/s. The device is completed by cathode 590, which comprises LiF (1 nm) and Al (100 nm) layers that are deposited (not depicted) successively at deposition rates of 0.015 nm/s and 0.3 nm/s, respectively.

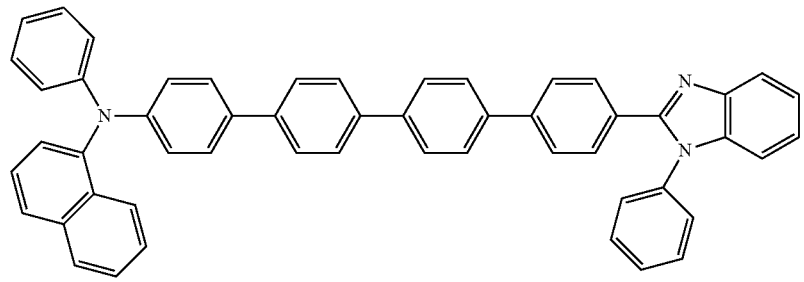

9-(4'''-(1-phenyl-1H-benzo[d]imidazol-2-yl)-[1,1':4',1'':4'',1'''-quaterphenyl]-4-yl)-9H-carbazole (Host-2)

FIG. 5 depicts the structure of a device that may be prepared as follows: SiN 520 covered glass substrates 510 are cleaned by ultrasound in detergent, deionized water, acetone, and 2-propanol consecutively, then baked at 110° C. for 3 hours, followed by treatment with oxygen plasma for 30 min. In a glove-box hosted vacuum deposition system at a pressure of 10$^{-7}$ torr, a hole-injecting layer of MoO$_3$ 530 is first deposited on top of the substrate at deposition rate of 0.05 nm/s, yielding a 10 nm thick film, a hole-transport layer of NPB 540 is then deposited on top of MoO$_3$ layer at deposition rate of 0.1 nm/s, yielding a 40 nm thick film. A 20 nm-thick light-emitting layer of Host-2 doped with 10 wt % red phosphorescent emitter Ir(piq)$_2$acac 550 is deposited on top of hole-transport layer. Afterwards a 0.4 nm-thick deposit of a plurality of nanostructures 560 (measured by the Quartz sensor) of TBB is deposited at deposition rate around 0.01 nm/s. Then a 40 nm-thick electron-transport layer of TPBi 580 is deposited at 0.1 nm/s and a 1 nm-thick electron injection layer of LiF 590 is deposited on top of TPBi at 0.015 nm/s. The device is completed by cathode, which comprises Mg:Ag (20 nm with ratio 1:3) mixed layer co-deposited at deposition rates of 0.1 nm/s and 0.3 nm/s, respectively.

Cyclic Voltammetry Experiments

Cyclic voltammetry (CV) experiments were performed with a µAuto-label potentiostat (Eco Chemie [Metrohm Autolab B.V., Utrecht, the Netherlands]). All measurements were carried out at room temperature with a conventional three-electrode configuration, e.g., a glassy carbon working electrode, a platinum auxiliary electrode, and a nonaqueous Ag/AgCl reference electrode. A sufficient amount of Compound 4 is added to achieve the desired concentration (e.g., $1.0\times10^{-4}$M) after addition to preprepared 0.1 M tetrabutylammonium hexafluorophosphate (n-Bu$_4$NPF$_6$) in DMF. The sample solution was prepared at room temperature and prior to measurement, and purged under argon for 5 mins. Then anodic potential up to 1.6 V (enough potential to contain oxidation potential of Compound 4) was applied to this test sample resulting in a test sample oxidation potential. Scan rate used was 100 mV/s. About 1.0 mg of ferrocene/ferrocenium was then added to the test sample at the end of each measurement for calibration and the oxidation potential measured again. From these oxidation potential spectra, the $E_{1/2}$ values were determined as ½ ($E_p^a+E_p^c$), where $E_p^a$ and $E_p^c$ are the anodic and cathodic peak potentials, respectively. HOMO (Highest occupied molecular orbital) energy was calculated by adding the determined shifted $E_{1/2}$ value with reference to ferrocene (4.8 eV).

A 10 ml sample of $10^{-6}$ M analyte, e.g., Compound 4, chloroform (CHCl$_3$) solution was analyzed witha a Cary 50 spectrophotometer (Varian, Inc. [Agilent Technologies, Santa Clara, Calif., USA]). Analyzing an absorption as a function of wavelength plot provided an observed optical onset (eV), providing an estimated Optical band gap value, Eg (Opt). LUMO (lowest unoccupied molecular orbital) energy was determined from the relation, Eg (Opt)=HOMO−LUMO. The results are reported below in Table 1.

TABLE 1

| Compound | HOMO (eV) | LUMO (eV) | Eg (opt) |
|---|---|---|---|
| Compound 4 | −6.35 | −2.7 | 3.65 |

Compound 4 (2 mg) was dissolved in 1 mL of 2-methylTHF (2-MeTHF) and then resulting solution was transferred into a quartz tube. Then the quartz tube containing Compound 4 was frozen (77K) by liquid nitrogen prior to measurement. Triplet ($T_1$) energy was measured by phosphorescent emission spectrum at 77K, using Fluoromax-3 spectrophotometer (Horiba Instruments, Irvine Calif., USA). The results of which are provided below in Table 2.

TABLE 2

| HTM | $T_1$ (eV) |
|---|---|
| Compound 4 | 2.62 |

Photoluminescence (PL) spectra were recorded on a FluoroMax-3 fluorescence spectrophotometer (Horiba Jobin Yvon, Edison, N.J., USA). 2-Methyltetrahydrofuran (2-MeTHF) (Aldrich, spectroscopic grade) was used as received. 2 M (2 mg of sample/1 mL of 2-MeTHF) was prepared and then transferred to quartz tube prior to measurement. Then, the sample was frozen by liquid nitrogen at 77K. Phosphorescent emission spectrum was recorded and the highest-energy vibronic band was determined to calculate triplet (T1) energy level.

Cyclic voltammetry (CV) was carried out in nitrogen-purged anhydrous N,N-dimethylformamide (DMF) (Aldrich) at room temperature with Echo-Chemie potentiostat/galvanostat (Echo Chemie/Metrohm Autolabe B.V., Utrecht, the Netherlands) Tetra-n-butylammonium hexafluorophosphate (TBAPF6) and DMF were purchased from Aldrich and used as received. Supporting electrolyte solution (0.1M) with TBAPF6 and analyte, e.g., Compound 4, (0.1 mM) in DMF was used for CV study. Formal potentials were calculated as the average of cyclic voltammetric anodic and cathodic peaks and ferrocenium-ferrocene (Fc+/Fc) as the internal standard was introduced to calibrate HOMO (highest occupied molecular orbital) and LUMO (lowest unoccupied molecular orbital) energy at each experiment. Scan rate of 100 mV/s was used unless otherwise.

Triplet (T1) Energy Calculation

Triplet energy was recorded on a FloroMax-3 spectrometer (Jobin Yvon Horiba, Edison, N.J.) with phosphorescence spectra at 77K. T1 was determined from the highest-energy vibronic sub-band of the phosphorescence spectra. For examples, Compound 4 showed a peak at 475 nm (indicated by red arrow) as the highest-energy band and its wavelength was then converted to a triplet energy of 2.62 eV.

HOMO/LUMO Energy Calculation:

HOMO energy was directly determined by oxidation potential of Compound 4 with respect to redox of ferrocene/ferrocenium in anodic scan in DMF. The difference between the oxidation potential of Compound 4 with respect to ferrocene/ferocenium was determined to be 1.55 eV. Therefore, using vacuum level of ferrocene as 4.8 eV, HOMO was determined to be −6.35 eV. LUMO energy was determined by equation of band gap Eg(eV)=HOMO−LUMO. Eg (eV) (3.65 eV) was estimated by onset value of UV-vis spectroscopy and then LUMO was calculated as −2.7 eV.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A light-emitting device comprising an anode, a cathode, a light-emitting layer disposed between the anode and the cathode, an electron-transport layer disposed between the cathode and the light-emitting layer, and a compound represented by a formula:

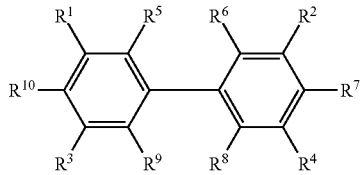

wherein $R^1$, $R^2$, $R^3$, and $R^4$ are independently optionally substituted benzoxazol-2-yl, optionally substituted benzothiazol-2-yl, or optionally substituted benzimidazol-2-yl, wherein any substituents of benzoxazol-2-yl, benzothiazol-2-yl, or benzimidazoly-2-yl are independently F, Cl, $CH_3$, $CF_3$, CN, $OCH_3$, $NH_2$, $NO_2$, $CO_2H$, CHO, or OH;

$R^5$, $R^6$, $R^7$, $R^8$, $R^9$, and $R^{10}$ are independently H, F, Cl, $CH_3$, $CF_3$, CN, $OCH_3$, $NH_2$, $NO_2$, $CO_2H$, CHO, or OH;

wherein the compound forms a nanostructure material disposed on the light-emitting layer between the light-emitting layer and the electron-transport layer; and wherein the nanostructure material has a periodicity on the light-emitting layer of between about 0.001 µm to about 20 µm.

2. The device of claim 1, wherein $R^1$ is optionally substituted benzoxazol-2-yl.

3. The device of claim 2, wherein the benzoxazol-2-yl is unsubstituted.

4. The device of claim 1, wherein $R^2$ is optionally substituted benzoxazol-2-yl.

5. The device of claim 4, wherein the benzoxazol-2-yl is unsubstituted.

6. The device of claim 1, wherein $R^3$ is optionally substituted benzoxazol-2-yl.

7. The device of claim 6, wherein the benzoxazol-2-yl is unsubstituted.

8. The device of claim 1, wherein $R^4$ is optionally substituted benzoxazol-2-yl.

9. The device of claim 8, wherein the benzoxazol-2-yl is unsubstituted.

10. The device of claim 1, wherein the compound is:

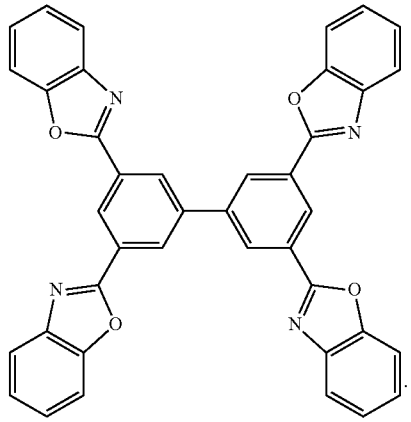 [SMILES: c1ccc2oc(-c3cc(-c4cc(-c5nc6ccccc6o5)cc(-c5nc6ccccc6o5)c4)cc(-c4nc5ccccc5o4)c3)nc2c1]

11. The device of claim 1, wherein the compound is:

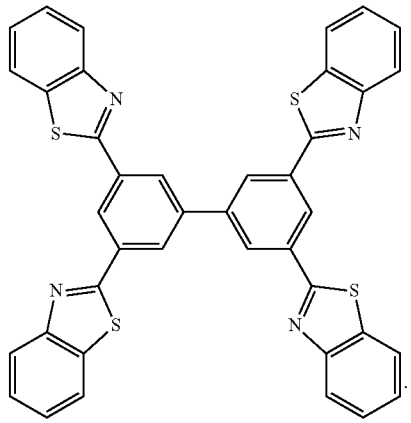

12. A light-emitting device comprising an anode, a cathode, a light-emitting layer disposed between the anode and the cathode, and a compound that is an optionally substituted 3,5,3',5'-tetra(benzoxazol-2-yl)biphenyl; an optionally substituted 3,5,3',5'-tetra(benzothiazol-2-yl)biphenyl; or an optionally substituted 3,5,3',5'-tetra(benzoimidazol-2-yl)biphenyl; wherein the compound forms a nanostructure material disposed on the light-emitting layer; and wherein the nanostructure material has a periodicity of between about 0.001 µm to about 20 µm.

13. The device of claim 12, wherein each substituent of the compound independently has a molecular weight of 15 g/mol to 200 g/mol.

14. The device of claim 13, wherein each substituent of the compound is independently F, Cl, $CH_3$, $CF_3$, CN, $OCH_3$, $NH_2$, $NO_2$, $CO_2H$, CHO, or OH.

15. The device of claim 12, wherein the compound has having 0, 1, 2, 3, or 4 substituents, wherein each substituent, if present, independently has a molecular weight of 15 g/mol to 200 g/mol.

16. The device of claim 12, wherein the compound has having 0, 1, or 2 substituents, wherein each substituent, if present, is independently F, Cl, $CH_3$, $CF_3$, CN, $OCH_3$, $NH_2$, $NO_2$, $CO_2H$, CHO, or OH.

17. The device of claim 12, wherein the nanostructure material has thickness of about 0.001 nm to about 10 nm.

18. A light-emitting device comprising an anode, a cathode, a light-emitting layer disposed between the anode and the cathode, and a nanostructure material deposited on the light-emitting layer, the nanostructure material consisting of a compound represented by a formula:

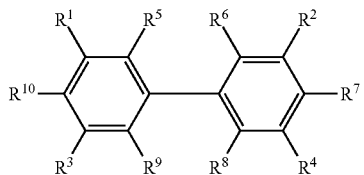

wherein $R^1$, $R^2$, $R^3$, and $R^4$ are independently optionally substituted benzoxazol-2-yl, optionally substituted benzothiazol-2-yl, or optionally substituted benzimidazol-2-yl, wherein any substituents of benzoxazol-2-yl, benzothiazol-2-yl, or benzimidazoly-2-yl are independently F, Cl, $CH_3$, $CF_3$, CN, $OCH_3$, $NH_2$, $NO_2$, $CO_2H$, CHO, or OH; and $R^5$, $R^6$, $R^7$, $R^8$, $R^9$, and $R^{10}$ are independently H, F, Cl, $CH_3$, $CF_3$, CN, $OCH_3$, $NH_2$, $NO_2$, $CO_2H$, CHO, or OH.

19. The device of claim 18, wherein the nanostructure material has a periodicity on the light-emitting layer of between about 0.001 μm to about 20 μm.

* * * * *